United States Patent [19]

Gafni et al.

[11] Patent Number: 5,191,896
[45] Date of Patent: Mar. 9, 1993

[54] APPARATUS FOR MEASURING THRESHOLD SENSITIVITY TO A STIMULUS

[75] Inventors: Ehud Gafni, Ramat Yishai; David Yarnitsky, Haifa, both of Israel

[73] Assignee: Medoc Ltd., Ramat Yishai, Israel

[21] Appl. No.: 722,666

[22] Filed: Jun. 28, 1991

[51] Int. Cl.$^5$ .............................................. A61B 5/00
[52] U.S. Cl. ................................... 128/742; 128/744; 606/27
[58] Field of Search ............... 128/742, 744, 739, 740, 128/741, 745, 746, 774; 606/27; 364/413.01, 413.02

[56] References Cited

U.S. PATENT DOCUMENTS

| | | | |
|---|---|---|---|
| 4,653,507 | 3/1987 | Laudadio | 128/742 |
| 4,763,666 | 8/1988 | Strian et al. | 128/742 |
| 5,007,433 | 4/1991 | Hermsdörffer et al. | 128/742 |
| 5,022,407 | 6/1991 | Horch et al. | 128/739 |

FOREIGN PATENT DOCUMENTS

2753109  6/1979  Fed. Rep. of Germany ...... 128/742

OTHER PUBLICATIONS

Navarro, X. et al., Evaluation of Thermal and Pain Sensitivity in Type I Diabetic Patients, J. of Neurology, Neurosurgery and Psychiatry 1991, 54, 60-64.
Jamal, G. A. et al., An Improved Automated Method for the Measurement of Thermal Thresholds. 1. Normal Subjects, J. of Nurology, Neurosurgery and Psychiatry, 1985, 48, 354-360.
Fowler, C. J. et al., A Portable System for Measuring Cutaneous Thresholds for Warming and Cooling, J. of Neurology, Neurosurgery and Psychiatry, 1987, 50, 1211 1215.
Ziegler, D. et al., Assesment of Small and Large Fiber Function in Long-Term Type 1 (insulin-dependent) Diabetic Patients With and Without Painful Neuropathy, Pain 34, 1988, 1-10.
Hiltz, C. D., et al., Thermal Discrimination Thresholds A comparison of Different Methods, Acta Neurol. Scand. 1990, 81, 533-540.
Yarnitsky, D., et al., Studies of Heat Pain Sensation in Man: Perception Thresholds, Rate of Stimulus Rise and Reaction Time, Pain, 40 1990.
Dyck, P. J., Limitations in Predicting Pathologic Abnormality of Nerves from the EMG Examination, Muscle and Nerve, 1990, 13, 371-375.
Claus, D., et al., Methods of Measurements of Thermal Thresholds, Acta Neurol. Scand. 1987, 76, 288-296.
Report and Recomendations of the San Antonio Conference on Diabetic Neuropathy, Annals of Neurology, 1988, 24, 99-104.
Kenshalo, D. R., Somesthetic Sensitivity in Young and Elderly Humans, J. of Gerontology, 1986, 41, 732-742.
Fruhstorfer, H. et al., Method for Quantitative Estimation of Thermal Thresholds in Patients, J. of Neurology, Neurosurgery and Psychiatry, 1976, 39, 1071-1075.
Arezzo, J. C. et al., Thermal Sensitivity Tester-Device for Quantitative Assessment of Thermal Sense in Diabetic Neuropathy, Diabetes, 1986, 35, 590-592.

Primary Examiner—Max Hindenburg
Assistant Examiner—Guy V. Tucker
Attorney, Agent, or Firm—Ladas & Parry

[57] ABSTRACT

Apparatus for measuring threshold sensitivity to a stimulus is disclosed. The apparatus includes sensory stimulation application apparatus for providing stimulus to a subject, computer apparatus for governing operation of the sensory stimulation application apparatus and operator interface apparatus for interfacing between an operator and the computer apparatus. The computer apparatus and the operator interface apparatus include apparatus for enabling an operator to selectably apply sensory stimulation to a patient minimally in accordance with any of the following protocols; method of limits, forced choice method; and staircase method. Other protocols which can be selected are Thermal Sensitivity Limen method and method of suprathreshold.

12 Claims, 11 Drawing Sheets

APPARATUS FOR MEASURING THRESHOLD SENSITIVITY TO A STIMULUS

FIELD OF THE INVENTION

The present invention relates to medical equipment generally and more particularly to apparatus for sensory and/or pain threshold measurement.

BACKGROUND OF THE INVENTION

There exist a number of known techniques for sensory threshold measurement in general and thermal threshold measurement in particular. These are described, inter alia in the following publications:

Goran A. Jamal et al "An Improved Automated Method for the Measurement of Thermal Thresholds. 1. Normal Subjects", *Journal of Neurology, Neurosurgery and Psychiatry* 1985; 48:354–360;

Clare J. Fowler et al "A Portable System for Measuring Cutaneous Thresholds for Warming and Cooling", *Journal of Neurology, Neurosurgery and Psychiatry* 1987; 50:1211–1215;

Dan Ziegler et al "Assessment of Small and Large Fiber Function in Long-term Type 1 (insulin-dependent) Diabetic Patients With and Without Painful Neuropathy" *Pain*, 34(1988) 1–10;

Claus D. Hilz et al "Thermal Discrimination Thresholds: A Comparison of Different Methods", *Acta Neurol Scand* 1990:81:533–540;

David Yarnitsky et al "Studies of Heat Pain Sensation in Man: Perception Thresholds, Rate of Stimulus Rise and Reaction Time", *Pain*, 40(1990) 85–91.

SUMMARY OF THE INVENTION

The present invention seeks to provide improved apparatus for measuring sensory or pain thresholds.

There is thus provided in accordance with a preferred embodiment of the present invention apparatus for measuring threshold sensitivity to a stimulus including sensory stimulation application apparatus for providing the stimulus to a subject, computer apparatus for governing operation of the sensory stimulation application apparatus and operator interface apparatus for interfacing between an operator and the computer apparatus. The computer apparatus and the operator interface apparatus including apparatus for enabling an operator to selectably apply the stimulus to a patient in accordance with any of the following protocols: method of limits; forced choice method; and staircase method. The threshold sensitivities are warm sensation, cold sensation, hot pain and cold pain.

Additionally, in accordance with an embodiment of the present invention, the computer apparatus and the operator interface apparatus includes apparatus for enabling an operator to selectably apply the stimulus to a patient also in accordance with either of the following protocols: Thermal Sensitivity Limen method and method of suprathreshold.

Further, in accordance with an embodiment of the present invention, the stimulus is temperature applied to a desired location on the subject's body and wherein the sensory stimulation application apparatus includes apparatus for changing the temperature.

Still further, in accordance with an embodiment of the present invention, the apparatus for changing the temperature can change the temperature at rates generally between 0.1° C./sec and 4° C./sec.

Moreover, in accordance with an embodiment of the present invention, the apparatus of the present invention also includes apparatus for performing age-normalized matching of results of a test.

Additionally, in accordance with an embodiment of the present invention, the apparatus of the present invention also includes apparatus for defining a new test protocol.

Furthermore, in accordance with an embodiment of the present invention, the apparatus for defining a new test application protocol include apparatus for defining desired parameters from among the following group of parameters: adaptation temperature, sensation or pain to be measured, rate of temperature change, number of trials per test, length of time between trials, manual or automatic triggering of the start of a next trial or test, providing sound at the start of a test, randomization of the order of trials and inclusion of catch trials.

Finally, in accordance with an embodiment of the present invention, the apparatus for defining a new test protocol includes apparatus for defining a default test or series of tests.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
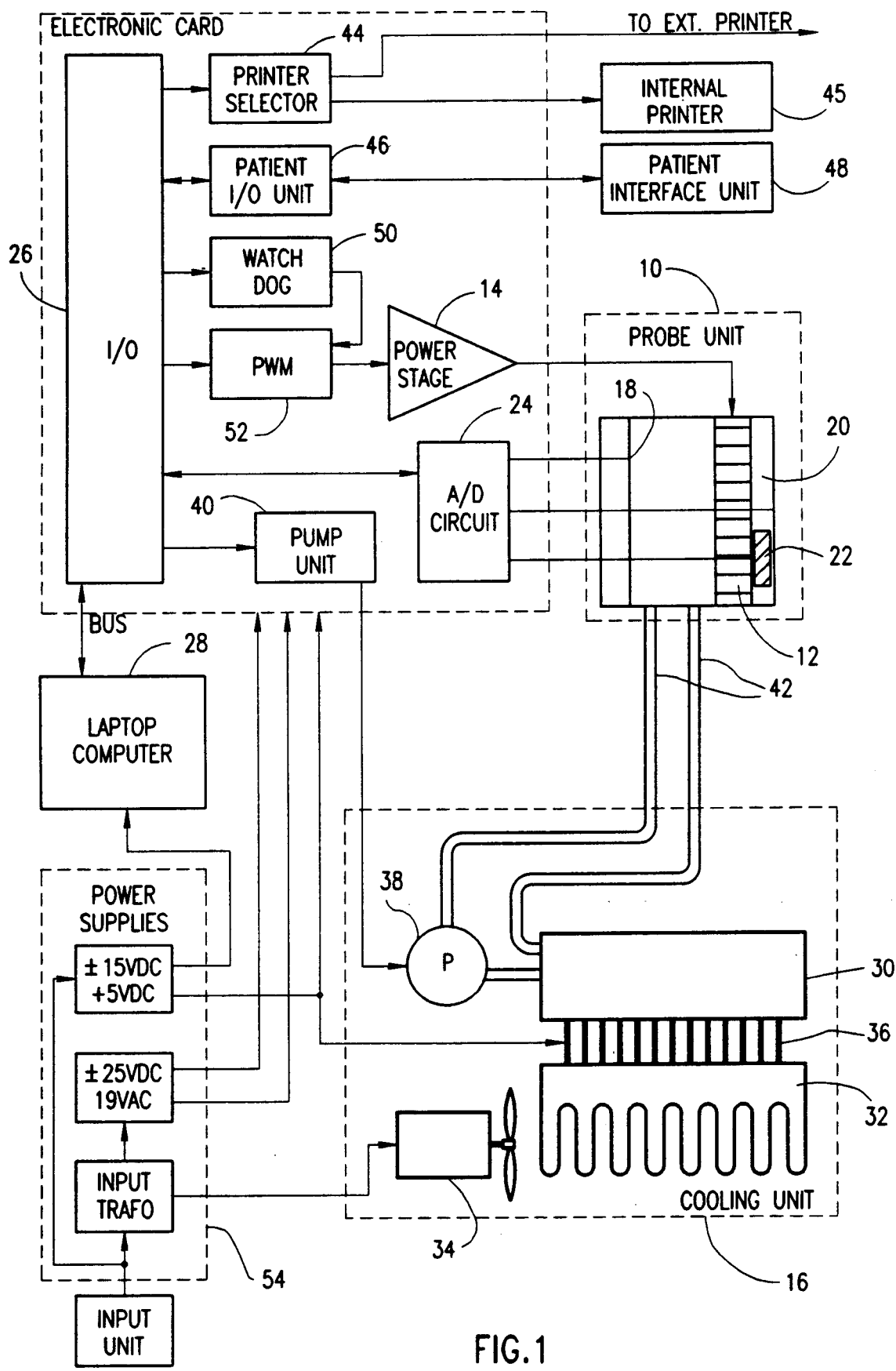
FIG. 1 is a generalized block diagram illustration of apparatus for measuring sensory and pain thresholds in accordance with a preferred embodiment of the present invention.
Figure 2A:
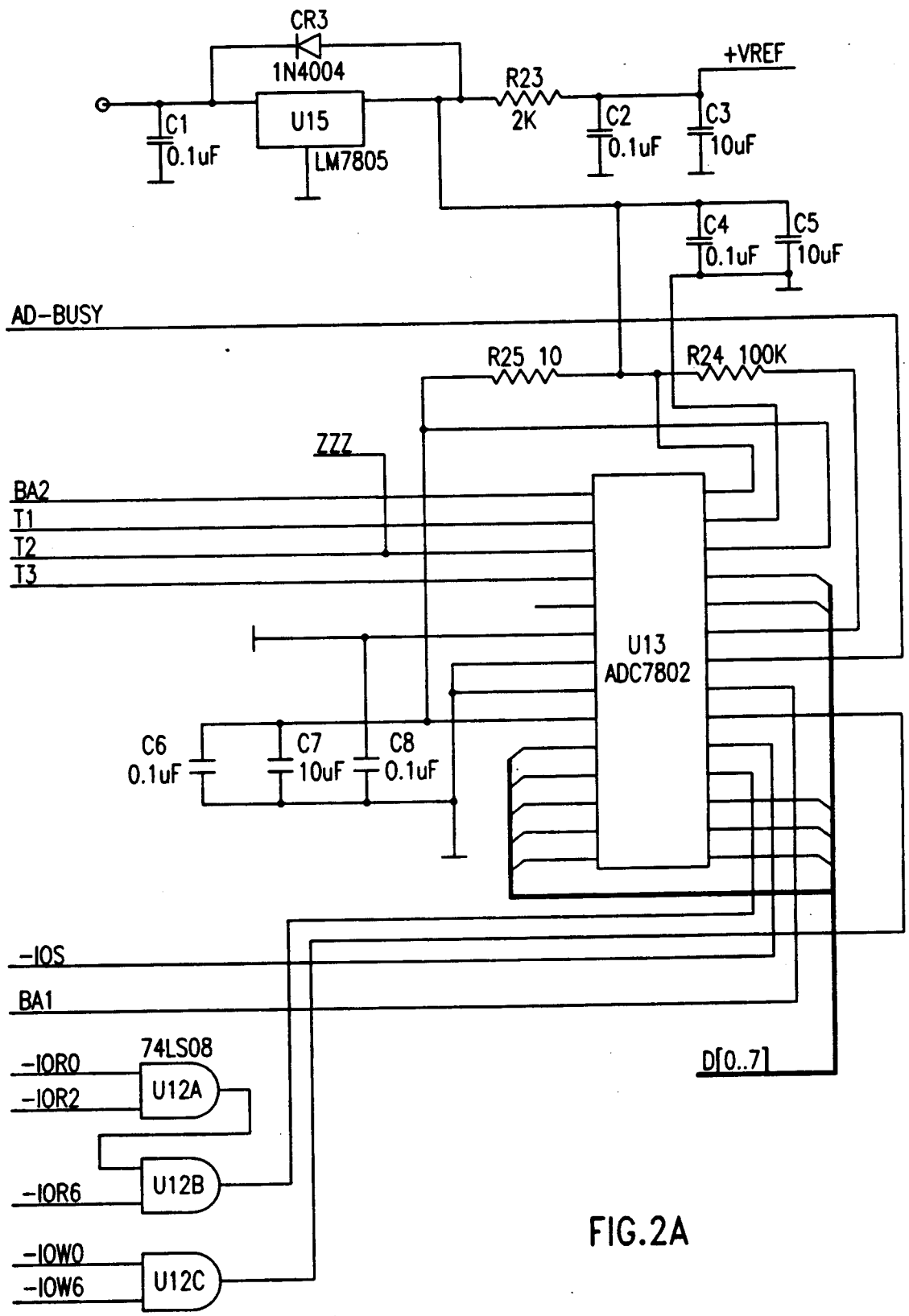
FIG. 2 is a detailed electrical schematic illustration of the apparatus of FIG. 1.
Figure 2B:
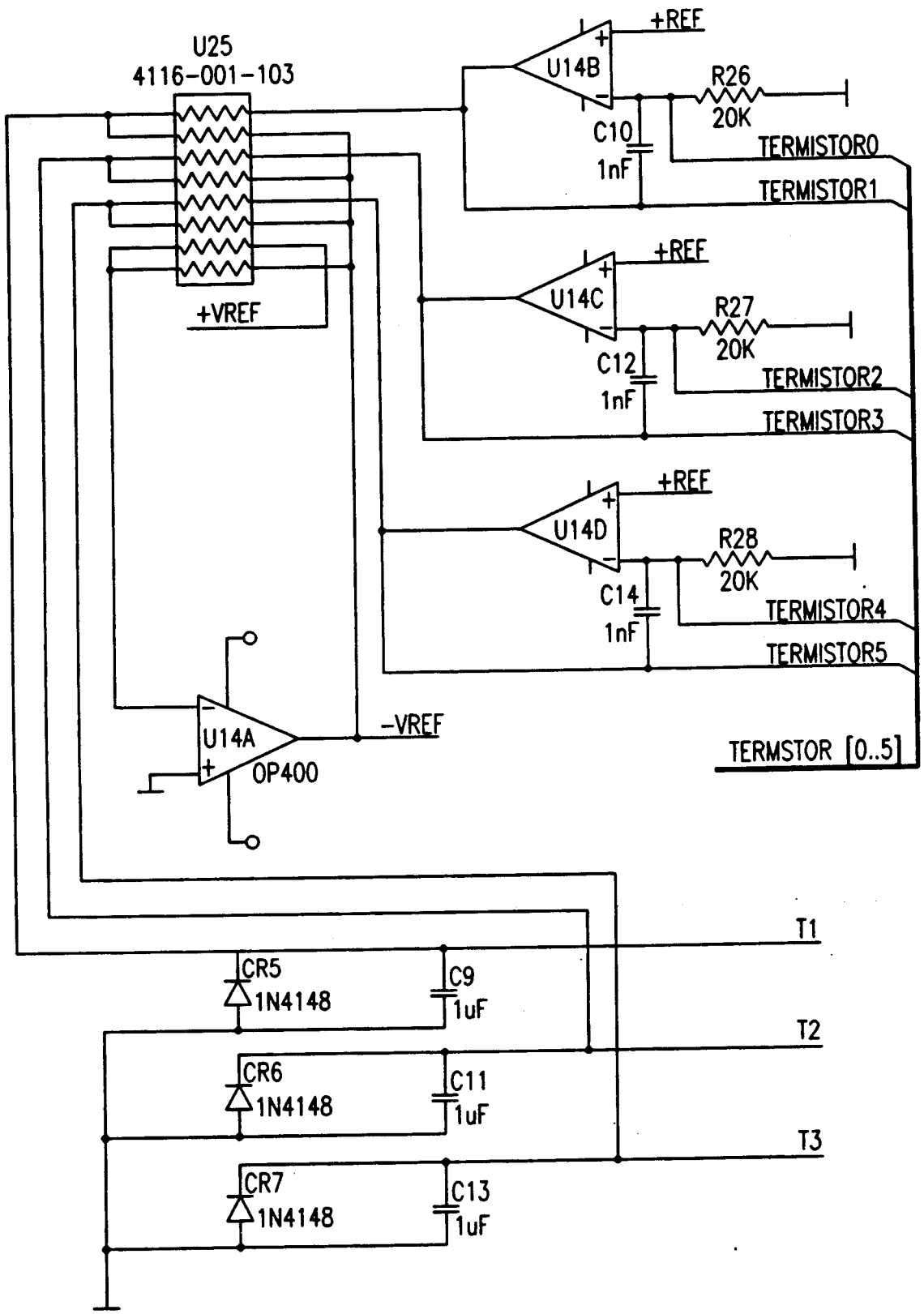
Figure 2C:
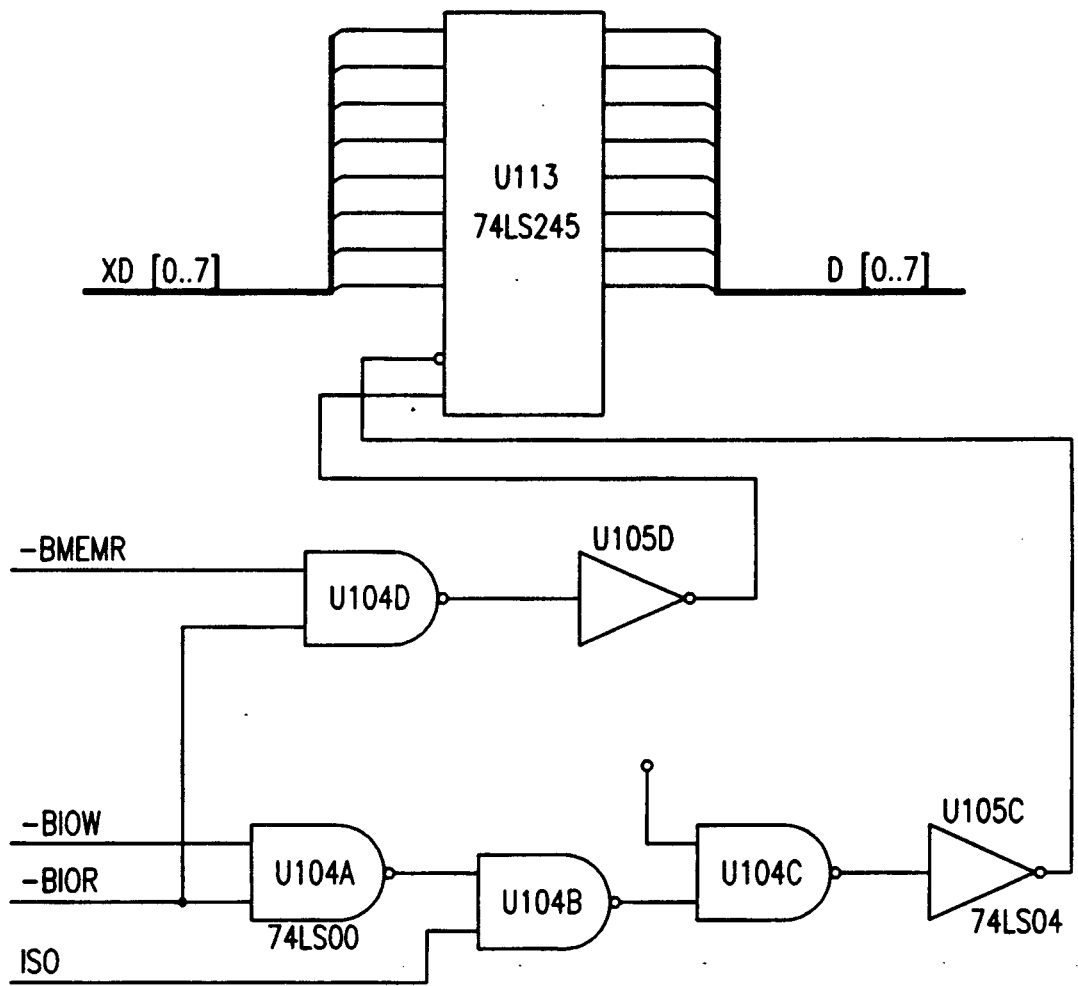
Figure 2D:
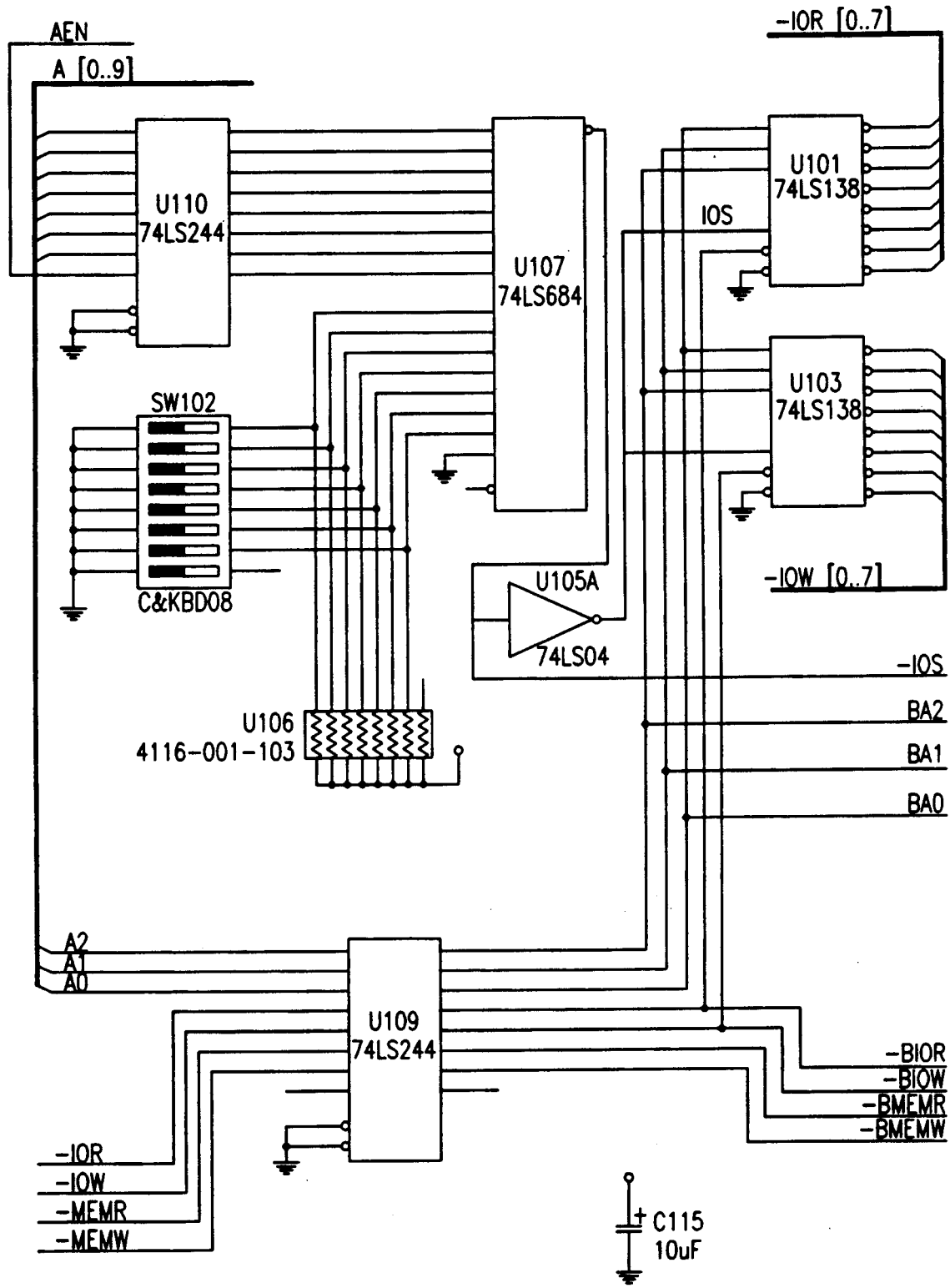
Figure 2E:
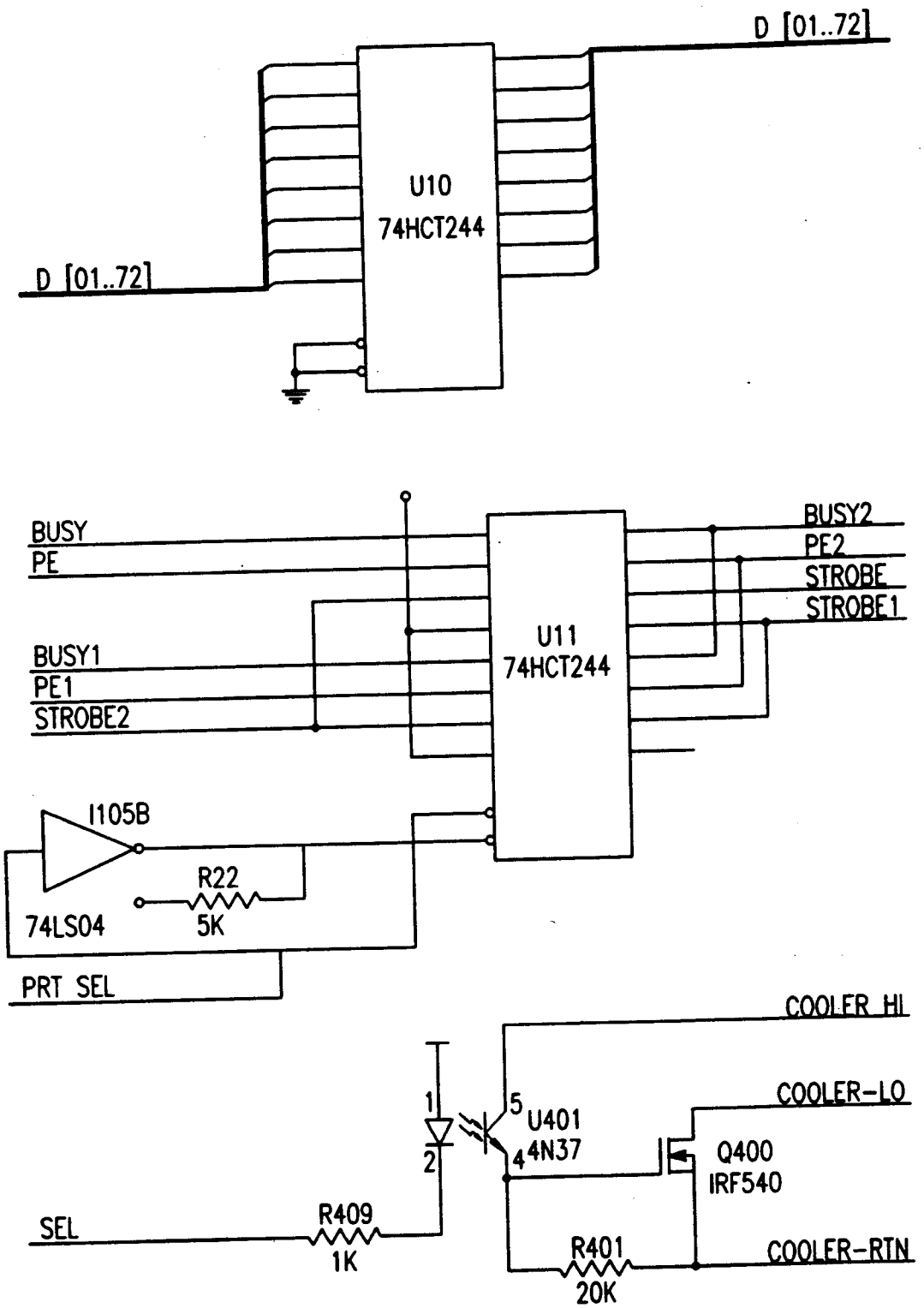
Figure 2F:
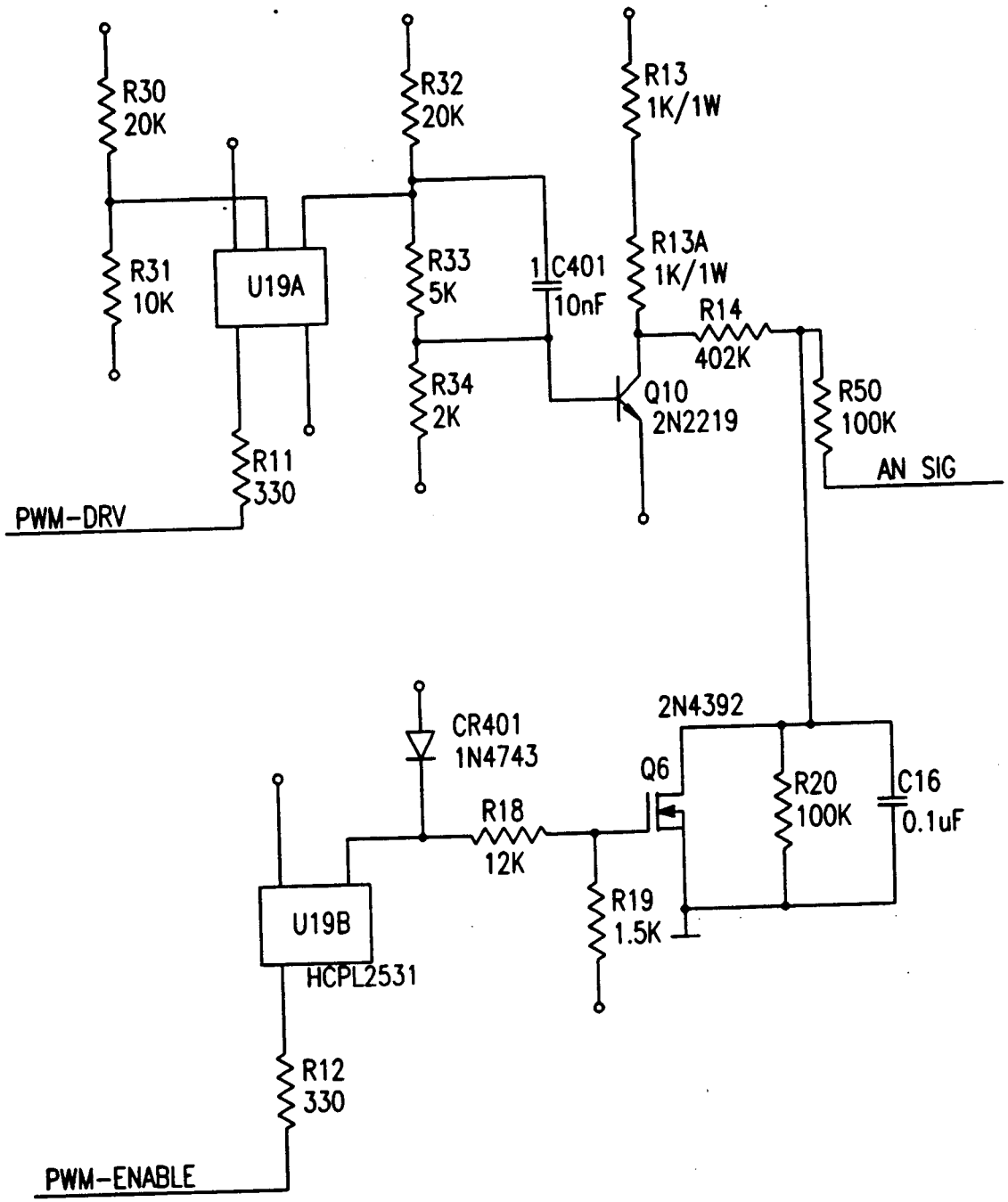
Figure 2G:
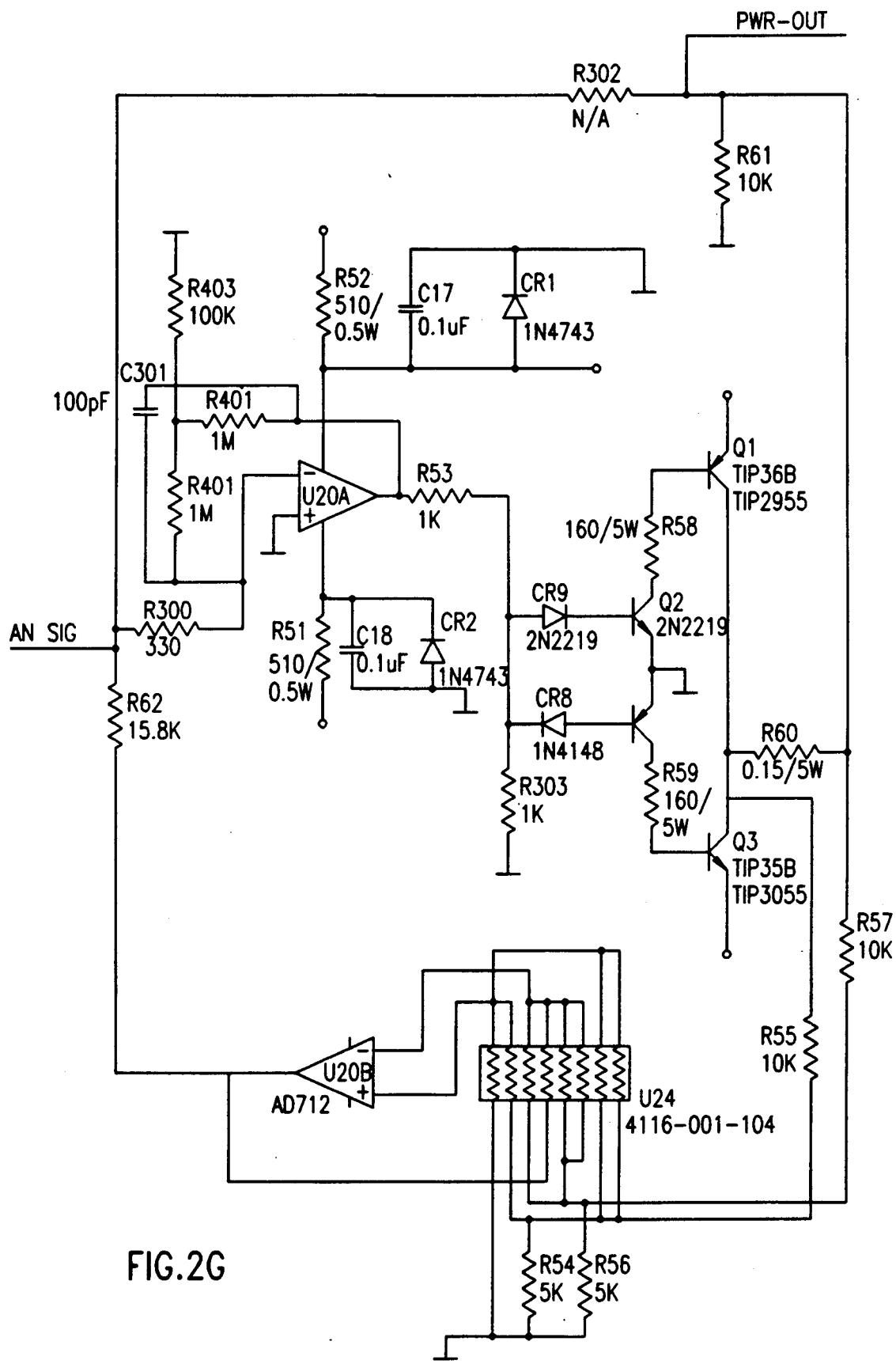
Figure 2H:
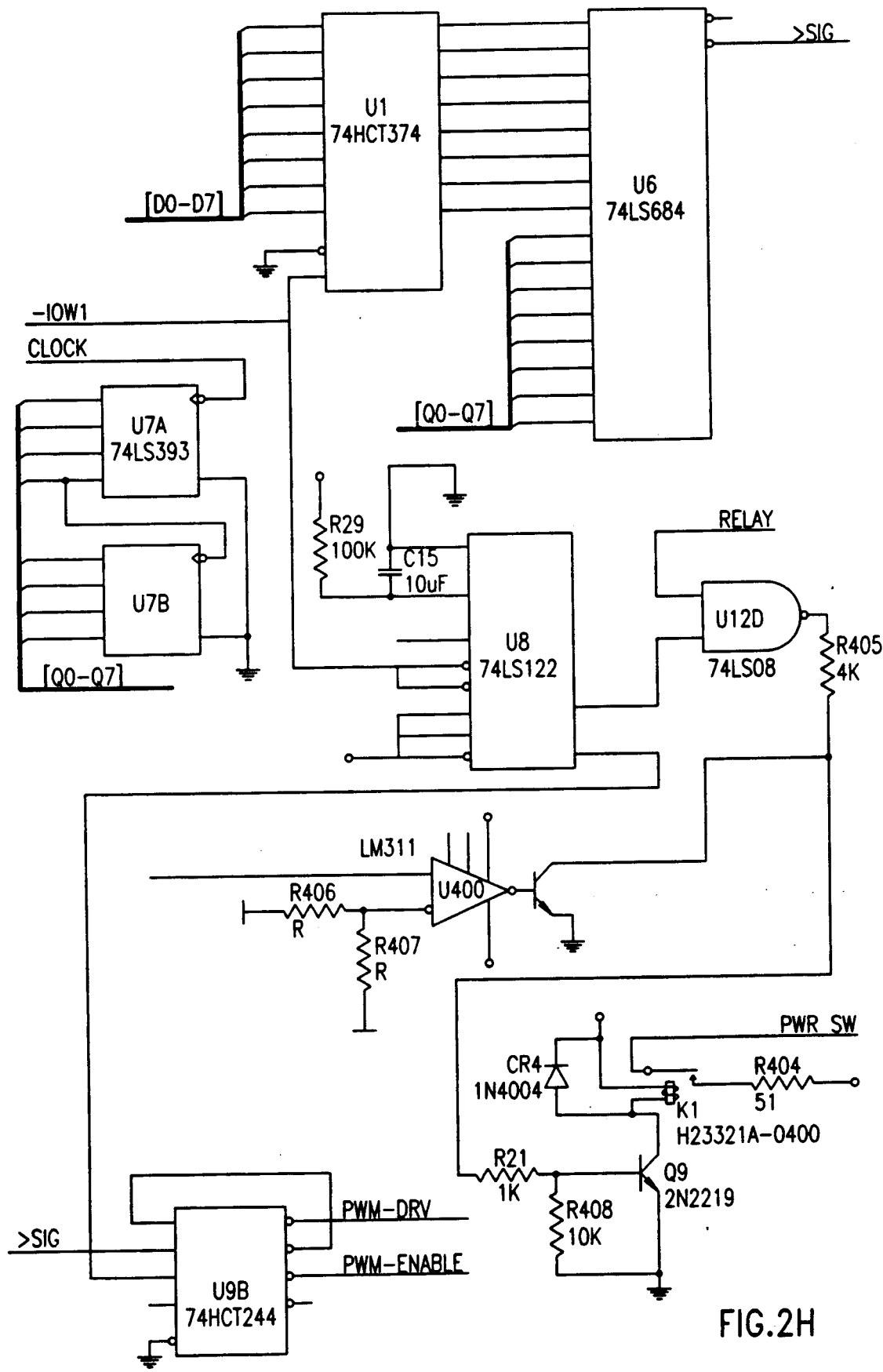
Figure 2I:
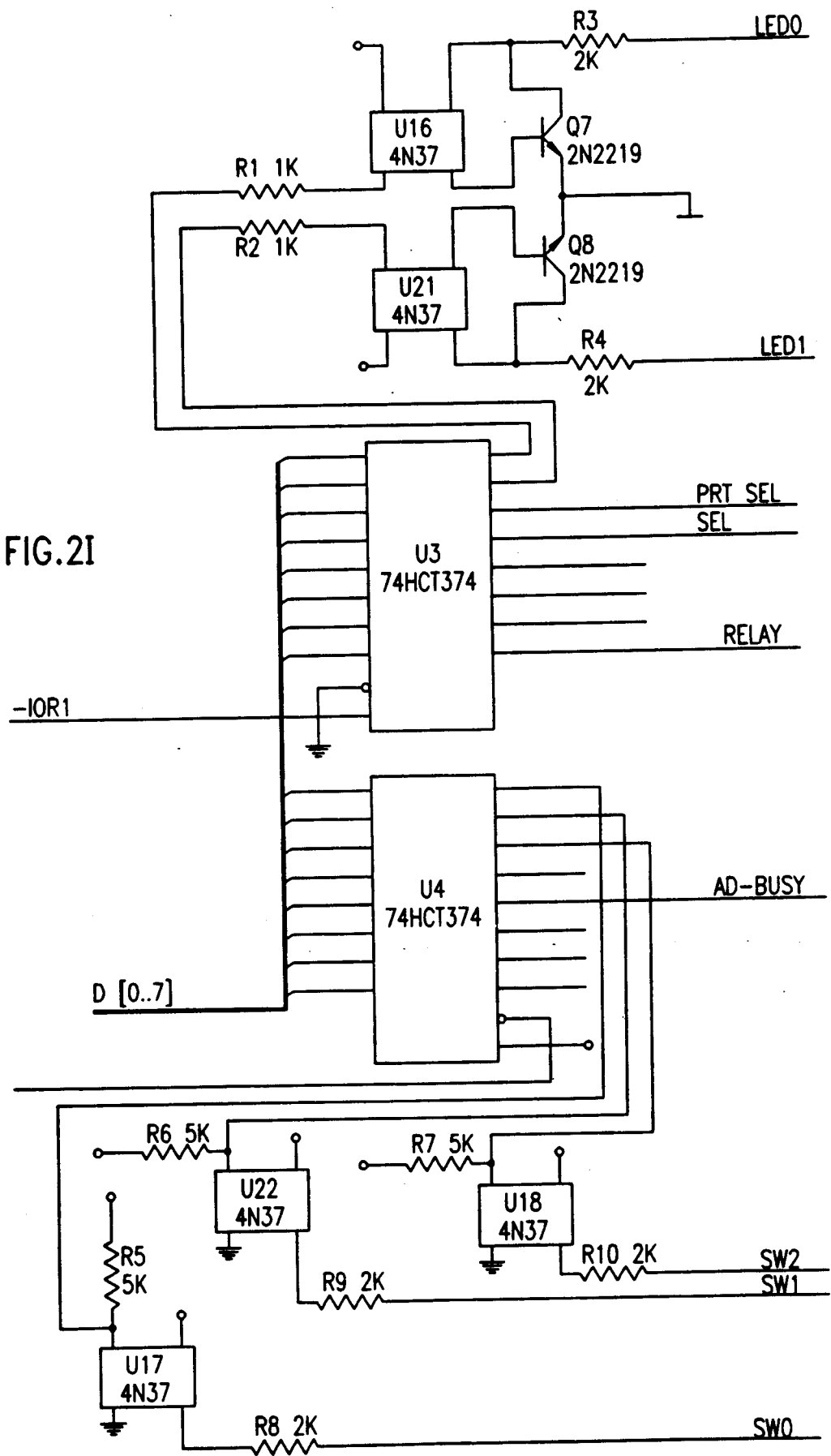

Reference is now made to FIGS. 1–3, which illustrate apparatus for measuring sensory and pain thresholds in accordance with a preferred embodiment of the present invention. The apparatus comprises at least one probe unit 10, also called a thermode, including a Peltier cooling/heating element 12 such as the MI1023T-03AC manufactured by Marlow Industries, Inc. of the U.S.A., which receives electrical power via a power amplifier 14 and is cooled by a cooling unit 16. Associated with the Peltier cooling/heating element 12 are a cooling water temperature sensor 18, a probe temperature sensor 20 and, optionally, a skin temperature sensor 22, all of which communicate via an A/D converter circuit 24 and an input/output interface 26, with a computer 28 such as a conventional laptop computer. Optionally, communications devices can be subsituted for computer 28 for communication with a computer already owned by an operator.

The cooling unit 16 comprises a heat exchanger 30, and a heat sink 32, with associated fan 34 associated, as illustrated, with a Peltier cooling element 36. A circulation pump 38, which receives electrical power via a pump control circuit 40, which is in turn controlled by computer 28 via input/output interface 26, circulates cooling fluid through conduits 42 extending between the probe unit 10 and heat exchanger 30.

In addition to the circuitry described above, the laptop computer 28 also controls via the input/output interface 26, a printer selector 44, which passes output information from the computer 28 to either an internal printer 45 or to an external printer (not shown).

Laptop computer 28 also controls via the input/output interface 26, a patient input/output unit 46, which communicates with a patient interface unit 48, such as a unit with two switches on it.

Laptop computer 28 also controls via the input/output interface 26, a temperature watch dog circuit 50, which operates a pulse width modulation circuit 52 which provides power to the probe via amplifier 14.

It will be appreciated that the apparatus of the present invention is typically packaged in a generally small unit.

A power supply 54, provides the necessary electrical power inputs to the various elements of the apparatus. The circuitry of FIG. 1 is fully described in the schematic of FIG. 2. Verbal description of the circuitry is considered to be unnecessary and redundant.

Figure 3C:
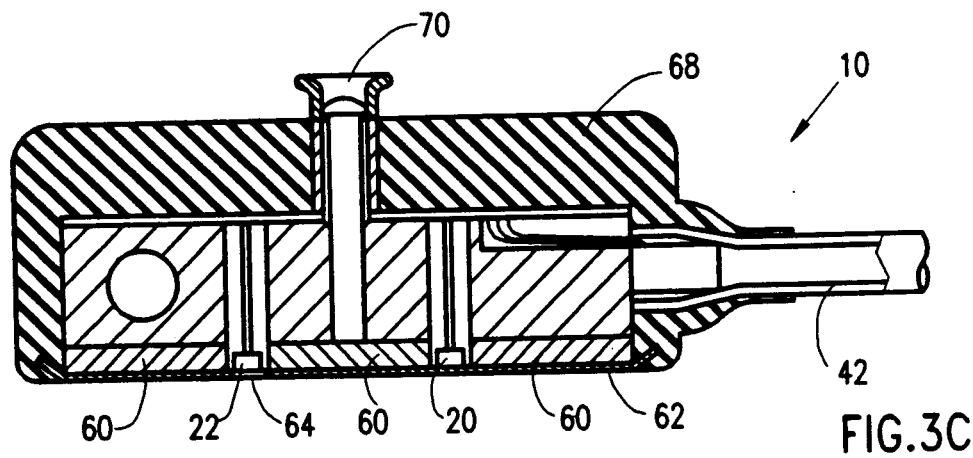
FIGS. 3A, 3B and 3C are top and two side view illustrations, respectively, of a probe forming part of the apparatus of FIG. 1.
Figure 3B:
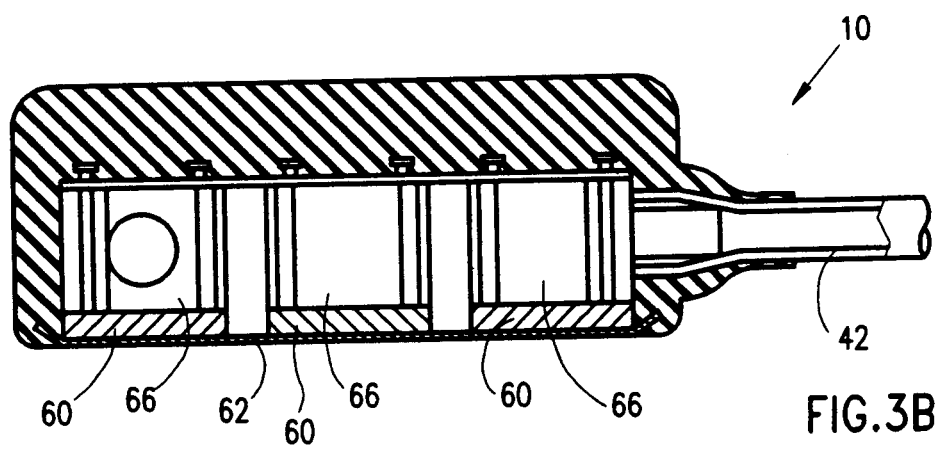
Figure 3A:
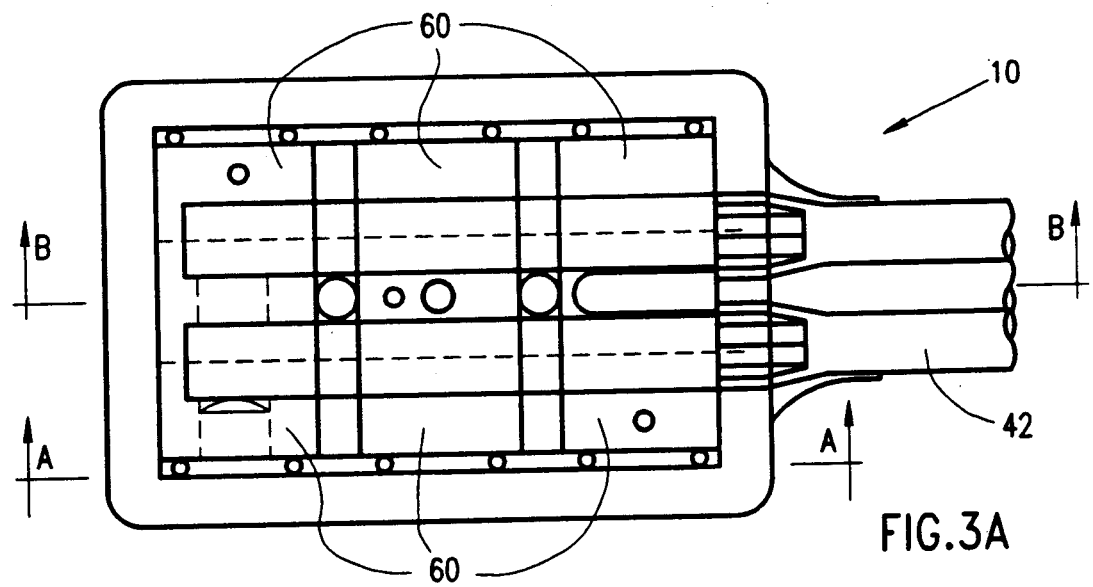

The probe unit 10 is illustrated in detail in FIGS. 3A, 3B and 3C. The probe unit 10 typically comprises at least one Peltier element 60 to be located close to the skin of a patient, covered by a plate 62, typically manufactured of aluminum. Six Peltier elements 60 are shown in FIG. 3A.

Between the Peltier elements 60 and next to the plate 62 are typically located a the probe temperature sensor 20 and, optionally, the skin temperature sensor 22. Skin temperature sensor 22 is located beneath plate 62 which has a hole 64 in it through which sensor 22 sense the skin temperature.

Heat exchangers 66 are typically located above the Peltier elements 60 and are operative to provide a temperature differential across Peltier elements 60. In order to enable rapid cooling and heating of the Peltier elements 60, heat exchangers 66 are typically maintained at a generally constant temperature, such as 32° C., through the operation of cooling unit 16. The probe unit 10 is typically able to provide a rate of change of temperature in the range of 0.1° C./sec to 4° C./sec although other, greater rates of temperature change are also possible. The rates of change of temperature typically vary in steps of 0.1° C./sec.

The heat exchangers 66 and Peltier elements 60 are surrounded on three sides by insulation 68, such as rubber, for maintaining the temperature of the heat exchangers 66 and for providing a housing to probe unit 10.

A cap 70 is additionally provided for connection to attaching apparatus (not shown), such as a belt, for attaching the probe unit 10 to the body of the patient.

The apparatus of the present invention performs the following measurement protocols: method of limits, forced choice method, Thermal Sensitivity Limen (TSL) method, method of staircase, and method of suprathreshold, for measuring thresholds of sensation of warm and cold and thresholds of pain due to heat and due to cold.

It will be noted that, for all measurements, the stimulus intensity is heat or cold. In heat and cold tests, the subject is asked to indicate when he first feels or ceases to feel heat. For pain measurements, he is asked to indicate when he first feels or ceases to feel pain.

In the method of limits protocol, described by Yarnitsky et al which article is incorporated herein by reference, for each trial, a stimulus intensity (either hot or cold) is steadily increased, at a selectable rate, from a reference adaptation temperature, typically 32° C., until a patient indicates, through patient interface unit 48, a point of change in the temperature of the probe unit 10. The stimulus intensity is typically then decreased to the adaptation temperature until a new trial is begun. Typically, a number of trials are performed and the threshold to the stimulus is typically defined as the average intensity of the trials.

It will further be appreciated that the method of limits requires that probe unit 10 be able to relatively quickly change stimulus intensities.

In the forced choice method, described by Jamal et al which article is incorporated herein by reference, the apparatus of the present invention presents a trial comprising two time periods, during one of which a stimulus is present and during the second no stimulus is present. At the end of the trial, the patient is asked to choose during which of the two time periods he felt a stimulus. If he is correct, the computer 28 scores the trial as a Success (S), otherwise, a score of Failure (F) is stored. The stimulus of the next trial will be either the same, or of longer or shorter duration in accordance with the Up-Down-Transform Rule (UDTR).

Alternatively, the trial is comprised of stimulating one of two probe units 10 and the patient has to indicate which probe unit 10 was activated.

The TSL method is described in the article by Navarro et al. "Evaluation of Thermal and Pain Sensitivity in Type I Diabetic Patients", *Journal of Neurology, Neurosurgery, and Psychiatry* 1991, Vol 54, pgs. 60-64, which article is incorporated herein by reference. In the TSL method, the probe is set to the adaptation temperature and the temperature increased at a steady rate until the patient indicates, through patient interface unit 48, that heat sensation or heat pain was felt. The temperature is then decreased until cold or cold pain is felt. The difference between the reversal points (e.g. points where the patient indicated a change in sensation or pain), over a number of trials, is called the TSL.

The staircase method is described in the article by Fowler et al which article is incorporated herein by reference. The probe unit 10 is brought to a predefined temperature level and the patient indicates, via patient interface unit 48, whether or not the stimulus was perceived. The temperature of the probe unit 10 is then brought to a second temperature level which is higher than the first temperature level if the patient indicated that no stimulus was perceived and lower than the first temperature level otherwise. The response of the patient is recorded after each trial. In this manner, an approximate threshold level is determined and is used to determine the range of temperatures to be provided during the second stage of the test.

In the second stage of the test, the temperature of the probe unit 10 is originally brought to a temperature above the level of the approximate threshold level. The patient is then provided with a series of dynamic thermal ramps to bring the temperature to a predetermined level. If the patient indicates that a stimulus was perceived, the next predetermined temperature level is reduced by one predetermined step level. If the patient indicates that no stimulus was perceived, the predetermined temperature level is increased, typically by a predefined step amount. The test terminates when a predetermined number of negative responses have been received. The patient threshold level is defined as the temperature level midway between the mean temperature of the positive responses and the mean temperature of the negative responses.

The suprathreshold method is described in the article by Price D.D., "Measurement of Pain: Sensory Discriminative Features", *Psychological and Neural Mechanisms of Pain*, Raven Press. NY, 1988, pp. 18-49. In the suprathreshold method, the extent of pain is measured. The temperature of the probe unit 10 is brought from the adaptation temperature to a level above the known threshold for pain (either hot or cold) for a predetermined length of time and then returned to the adaptation temperature. The patient is then asked to describe the intensity of the pain felt, where the intensity can be described by words, by a digital scale, typically varying between 0 and 10 where 0 represents no pain and 10 represents the maximal possible pain, or by a visual analog scale displayed on the screen of laptop computer 28.

In accordance with the present invention, the tests can be performed manually in which the operator have to indicate to laptop computer 28 to start a new trial, or automatically, in which the computer 28 begins a new trial after passage of a length of time set by the operator.

In accordance with the present invention, the results of a test can be compared to those for a normal population in accordance with the age of the patient. Results of tests with normal subjects, "normal data", can be stored in computer 28 in age blocks. If desired, the normal data can be that provided by the manufacturer or it may be data gathered by the operator during his own experiments.

The computer 28 is typically also operative to provide post-processing on the test data. This post-processing typically comprises mathematical analysis of the test data as is required by the testing method, graphical operations for graphically providing to the operator the results of the tests, comparing the results of the test to an age-normalized group or to previous results received for the patient in previous tests.

The apparatus of the present invention enables an operator to choose the appropriate threshold for sensation or pain to be measured, the appropriate location on the body of the patient to place the probe, and the appropriate protocol by which to measure it. Laptop computer 28 stores information regarding each patient as well as the results of each test performed. Furthermore, laptop computer 28 can present the results graphically and can compare them to age-matched normal values for the selected location on the body.

In accordance with the present invention, an operator can modify or define a desired test sequence by programming laptop computer 28 to provide any desired sequence of stimulus intensities and time intervals. The programmable parameters are typically adaptation temperature, sensation or pain to be measured, rate of temperature change, number of trials per test, length of time between trials, manual or automatic triggering of the start of a next trial or test, and providing sound at the start of a test. The order of trials can be randomized and the operator can choose to have trials during which no stimulation occurs. Such trials are known as "catch trials".

Furthermore, the computer 28 enables the operator to define a "default" test or series of tests which is the test or tests which will be run when a novice or non-operator is operating the apparatus of the present invention.

Annex A is source code of software running on laptop computer 28 for operating the apparatus of the present invention in the manner described hereinabove.

Annex B is a collection of typical screen displays preferably provided by the software of Annex A.

Annex C is a collection of typical instruction sets shown to the operator in connection with the screen displays of Annex B relating to programming a new type of test sequence.

It will be appreciated by persons skilled in the art that the present invention is not limited to what has been particularly shown and described hereinabove. Rather, the scope of the present invention is defined only by the claims that follow:

ANNEX A

```
'FILE :CONTLOOP.BAS
SUB ContLoop
    SHARED FilteredTemp,Tin,Tout&()

'READ A\D
    V1% = INP(560)
    V2% = INP(562)
    OUT 560,0

'CHECK BUSY SIGNAL
    IF V2% < 17 THEN
       V%=256*V2%+V1%
    ELSE
       V%=4000 'bussy -must not hapend
    END IF
    'CALCULATE OUTPUT
    FILTEREDTEMP=0.8*FILTEREDTEMP+Tout&(V%)/50000
    'FILTEREDTEMP=0.8*FILTEREDTEMP+0.2*Tin 'demo version
    LOOPERROR=Tin-FILTEREDTEMP' POLARITY FITS PCB (NOT WW)
    A%=INT(20*LOOPERROR)
    IF A%>127 THEN A% = 127
    IF A% < -127 THEN A% = -127
    B%=A%+128
    OUT 561,B%
END SUB SUB DecEdit(R%,C%,L%,S$,E$)
LOCATE R%,C% : COLOR 0,7 :IF S$="" THEN S$=STRING$(L%,32)
PRINT S$
ExitDecEdit%=%False
```

```
DO UNTIL ExitDecEdit%
  LOCATE R%,C%+L%-1
  CALL GetChar(E$,A$)
  SELECT CASE E$
    CASE "DIGIT"
      S$=S$+A$
      IF LEN(S$)>L% THEN S$=RIGHT$(S$,L%)
      LOCATE R%,C% : PRINT S$
    CASE "CHAR"
      IF ASC(A$)=46 THEN
        S$=S$+A$
        IF LEN(S$)>L% THEN S$=RIGHT$(S$,L%)
        LOCATE R%,C% : PRINT S$
      END IF
    CASE "DEL"
      S$=STRING$(L%,32)
      LOCATE R%,C% : PRINT S$
    CASE "UP","DOWN","CR","ESC","LEFT","RIGHT","INS"
      ExitDecEdit%=%True
  END SELECT
LOOP
LOCATE R%,C% :COLOR 7,0 : PRINT S$
END SUB
SUB EngEdit(R%,C%,L%,S$,E$)
LOCATE R%,C% : COLOR 0,7 : S$=S$+STRING$(L%-LEN(S$),32)
PRINT S$
COUNT%=1% : ExitEngEdit%=%False
DO UNTIL ExitEngEdit%
  LOCATE R%,C%+COUNT%-1 :COLOR 16,7
  IF MID$(S$,COUNT%,1)=" " THEN
    PRINT "_"
  ELSE
    PRINT MID$(S$,COUNT%,1)
  END IF
  COLOR 0,7
  CALL GetChar(E$,A$)
  LOCATE R%,C%:PRINT S$
  SELECT CASE E$
    CASE "DIGIT","CHAR"
      S$=LEFT$(S$,COUNT%-1)+A$+RIGHT$(S$,L%-COUNT%)
      LOCATE R%,C% : PRINT S$
      IF COUNT%<L% THEN INCR COUNT%
    CASE "LEFT"
      IF COUNT%>1 THEN DECR COUNT%
    CASE "RIGHT"
      IF COUNT%<L% THEN INCR COUNT%
    CASE "UP","DOWN","CR","ESC"
      ExitEngEdit%=%True
  END SELECT
LOOP
LOCATE R%,C% :COLOR 7,0 : PRINT S$
Done%=%False
Blanks%=0
DO UNTIL Done%
  IF Blanks%<L% THEN
    IF MID$(S$,L%-Blanks%,1)=CHR$(32) THEN
      DECR Blanks%
    ELSE
      Done%=%True
    END IF
  ELSE
    Done%=%True
  END IF
LOOP
IF Blanks%=L% THEN
  S$=""
ELSE
  S$=LEFT$(S$,L%-Blanks%)
END IF
END SUB

'FILE : FC_EDIT.BAS

SUB FCEdit(FCNr%,ScreenCounter%)
```

```
SHARED ForcedName$(),ForcedDesc$(),ForcedAdap%()
SHARED ForcedMode%(),ForcedRate%(),ForcedInt%()
SHARED ForcedFirst%(),ForcedSecond%(),ForcedThird%()
SHARED ForcedTrig%(),ForcedSound%(),ForcedCatch%()
SHARED TotalForced%

Modality$(1)="CS"
Modality$(2)="WS"

TempName$=ForcedName$(FCNr%)
TempDesc$=ForcedDesc$(FCNr%)
TempAdap$=RIGHT$(STR$(ForcedAdap%(FCNr%)/10),4)
TempAdap$=STRING$(4-LEN(TempAdap$),32)+TempAdap$
TempMode%=ForcedMode%(FCNr%)
TempRate$=RIGHT$(STR$(ForcedRate%(FCNr%)/10),4)
TempRate$=STRING$(4-LEN(TempRate$),32)+TempRate$
TempInt$= RIGHT$(STR$(ForcedInt%(FCNr%)),2)
IF LEN (TempInt$)=1 THEN TempInt$= " "+TempInt$
TempFirst$= RIGHT$(STR$(ForcedFirst%(FCNr%)/10),4)
TempFirst$=STRING$(4-LEN(TempFirst$),32)+TempFirst$
TempSecond$= RIGHT$(STR$(ForcedSecond%(FCNr%)/10),4)
TempSecond$=STRING$(4-LEN(TempSecond$),32)+TempSecond$
TempThird$= RIGHT$(STR$(ForcedThird%(FCNr%)/10),4)
TempThird$=STRING$(4-LEN(TempThird$),32)+TempThird$
IF ForcedTrig%(FCNr%)=%False THEN
   TempTrig$=" NO"
  ELSE
   TempTrig$="YES"
END IF
IF ForcedSound%(FCNr%)=%False THEN
   TempSound$=" NO"
  ELSE
   TempSound$="YES"
END IF
IF ForcedCatch%(FCNr%)=%False THEN
   TempCatch$=" NO"
  ELSE
   TempCatch$="YES"
END IF
LOCATE 3,5:PRINT "NAME:":LOCATE 3,12    :PRINT TempName$
LOCATE 4,5:PRINT "DESCR:":LOCATE 4,12   :PRINT TempDesc$
LOCATE 7,5:PRINT "ADAPTATION TEMP:"     :LOCATE 7,32:PRINT TempAdap$
LOCATE 8,5:PRINT "MODALITY:"
LOCATE 8,34:IF TempMode%<>0 THEN Print Modality$(TempMode%)
LOCATE 9,5:PRINT "TEMP RATE(deg/sec):"  :LOCATE 9,32:PRINT TempRate$
LOCATE 10,5:PRINT "INTERVAL (sec):"     :LOCATE 10,34:PRINT TempInt$
LOCATE 11,5:PRINT "COARSE SEARCH STEP"  :LOCATE 11,32:PRINT TempFirst$
LOCATE 12,5:PRINT "INTERMEDIATE SEARCH STEP":LOCATE 12,32:PRINT TempSecond$
LOCATE 13,5:PRINT "FINE SEARCH STEP"    :LOCATE 13,32:PRINT TempThird$
LOCATE 14,5:PRINT "MAN. TRIG. OPTION:"  :LOCATE 14,33:PRINT TempTrig$
LOCATE 15,5:PRINT "SOUND OPTION:"       :LOCATE 15,33:PRINT TempSound$
LOCATE 16,5:PRINT "DUMMY TEST OPTION:"  :LOCATE 16,33:PRINT TempCatch$ LOCATE 18,5:PRINT "SAVE PROGRAM"
LOCATE 19,5:PRINT "RETURN TO FORCED CHOICE TESTS LIST (ABANDON PROGRAM)"
LOCATE 20,5:PRINT "RETURN TO MAIN MENU (ABANDON PROGRAM)"

InputField%=1 :
ExitFCEdit%=%False
DO UNTIL ExitFCEdit%
  SELECT CASE InputField%
    CASE 1 'NAME
        CALL Instruction(1,"input or modify test name")
        CALL Instruction(2,"")
        CALL EngEdit(3,12,20,TempName$,ExitCode$)
    CASE 2 'description
        CALL Instruction(1,"input or modify test description")
        CALL Instruction(2,"")
        CALL EngEdit(4,12,40,TempDesc$,ExitCode$)
    CASE 3 'temp
        CALL Instruction(1,"input or modify adaptation temperature")
        CALL Instruction(2,"")
        CALL DecEdit(7,32,4,TempAdap$,ExitCode$)
    CASE 4 '
        CALL Instruction(1,"toggle WS/CS using TAB key")
        CALL Instruction(2,"WS = warm sensation   CS = cold sensation")
        LOCATE 8,34:COLOR 0,7
```

```
    IF TempMode%<>0 THEN Print Modality$(TempMode%) ELSE PRINT " "
    CALL GetChar(ExitCode$,A$)
    IF ExitCode$="TAB" THEN INCR TempMode%
    IF TempMode%>2 THEN TempMode%=1
    LOCATE 8,34:COLOR 7,0
    IF TempMode%<>0 THEN Print Modality$(TempMode%) ELSE PRINT " "
  CASE 5 '
    CALL Instruction(1,"input or modify temperature rate")
    CALL Instruction(2,"")
    CALL DecEdit(9,32,4,TempRate$,ExitCode$)
  CASE 6 '
    CALL NatEdit(10,34,2,TempInt$,ExitCode$)
    CALL Instruction(1,"input or modify time interval")
    CALL Instruction(2,"")
  CASE 7 '
    CALL Instruction(1,"input or modify step size")
    CALL Instruction(2,"")
    CALL DecEdit(11,32,4,TempFirst$,ExitCode$)
  CASE 8 '
    CALL Instruction(1,"input or modify step size")
    CALL Instruction(2,"")
    CALL DecEdit(12,32,4,TempSecond$,ExitCode$)
  CASE 9 '
    CALL Instruction(1,"input or modify step size")
    CALL Instruction(2,"")
    CALL DecEdit(13,32,4,TempThird$,ExitCode$)
  CASE 10 '
    CALL Instruction(1,"toggle YES/NO using TAB key")
    CALL Instruction(2,"")
    CALL BinEdit(14,33,"YES"," NO",TempTrig$,ExitCode$)
  CASE 11 '
    CALL Instruction(1,"toggle YES/NO using TAB key")
    CALL Instruction(2,"")
    CALL BinEdit(15,33,"YES"," NO",TempSound$,ExitCode$)
  CASE 12 '
    CALL Instruction(1,"toggle YES/NO using TAB key")
    CALL Instruction(2,"")
    CALL BinEdit(16,33,"YES"," NO",TempCatch$,ExitCode$)
  CASE 13 'save
    CALL Instruction(1,"")
    CALL Instruction(2,"")
    COLOR 0,7
    LOCATE 18,5:PRINT "SAVE PROGRAM"
    CALL GetChar(ExitCode$,A$)
    COLOR 7,0
    LOCATE 18,5:PRINT "SAVE PROGRAM"
  CASE 14'return to forced choice menu
    CALL Instruction(1,"")
    CALL Instruction(2,"")
    COLOR 0,7
    LOCATE 19,5:PRINT "RETURN TO FORCED CHOICE TESTS LIST (ABANDON PROGRAM)"
    CALL GetChar(ExitCode$,A$)
    COLOR 7,0
    LOCATE 19,5:PRINT "RETURN TO FORCED CHOICE TESTS LIST (ABANDON PROGRAM)"
  CASE 15'return to main menu
    CALL Instruction(1,"")
    CALL Instruction(2,"")
    COLOR 0,7
    LOCATE 20,5:PRINT "RETURN TO MAIN MENU (ABANDON PROGRAM)"
    CALL GetChar(ExitCode$,A$)
    COLOR 7,0
    LOCATE 20,5:PRINT "RETURN TO MAIN MENU (ABANDON PROGRAM)"
END SELECT SELECT CASE ExitCode$
  CASE "UP"
    SELECT CASE InputField%
      CASE 2 TO 15
        DECR InputField%
    END SELECT
  CASE "DOWN"
    SELECT CASE InputField%
      CASE 1 TO 14
        INCR InputField%
    END SELECT
```

```
     CASE "CR"
        SELECT CASE InputField%
           CASE 1 TO 12
              INCR InputField%
           CASE 13 'SAVE 'TEST DATA
              DataTested%=%True
              IF TempName$ ="" THEN DataTested%=%False:InputField%=1
              IF VAL(TempAdap$)>35 OR VAL(TempAdap$)<25 THEN
                 DataTested%=%False:InputField%=3
              END IF
              IF TempMode%=0 THEN  DataTested%=%False:InputField%=4
              IF VAL(TempRate$)=0 THEN DataTested%=%False:InputField%=5
              IF VAL(TempInt$)=0 THEN DataTested%=%False:InputField%=7

IF DataTested%=%True THEN
                 ForcedName$(FCNr%)=TempName$
                 ForcedDesc$(FCNr%)=TempDesc$
                 ForcedAdap%(FCNr%)=VAL(TempAdap$)*10
                 ForcedMode%(FCNr%)=TempMode%
                 ForcedRate%(FCNr%)=VAL(TempRate$)*10
                 ForcedInt%(FCNr%)=VAL(TempInt$)
                 ForcedFirst%(FCNr%)=VAL(TempFirst$)*10
                 ForcedSecond%(FCNr%)=VAL(TempSecond$)*10
                 ForcedThird%(FCNr%)=VAL(TempThird$)*10
                 IF TempTrig$=" NO" THEN
                    ForcedTrig%(FCNr%)=%False
                   ELSE
                    ForcedTrig%(FCNr%)=%True
                   END IF
                   IF TempSound$=" NO" THEN
                      ForcedSound%(FCNr%)=%False
                     ELSE
                      ForcedSound%(FCNr%)=%True
                   END IF
                   IF TempCatch$=" NO" THEN
                      ForcedCatch%(FCNr%)=%False
                     ELSE
                      ForcedCatch%(FCNr%)=%True
                   END IF
                 IF FCNr%>TotalForced% THEN INCR TotalForced%
                 OPEN "FORCED.TSA" FOR OUTPUT AS #1
                 WRITE #1 ,TotalForced%
                 FOR I%=1 TO TotalForced%
                    WRITE #1, ForcedName$(I%),ForcedDesc$(I%),ForcedAdap%(I%)
                    WRITE #1,ForcedMode%(I%),ForcedRate%(I%),ForcedInt%(I%)
                    WRITE #1,ForcedFirst%(I%),ForcedSecond%(I%),ForcedThird%(I%)
                    WRITE #1,ForcedTrig%(I%),ForcedSound%(I%),ForcedCatch%(I%)
                 NEXT I%
                 CLOSE #1
                 ScreenCounter%=0
                 ExitFCEdit%=%True END IF
           CASE 14' return to forced choice
              DECR ScreenCounter%
              ExitfcEdit%=%True
           CASE 15
              ScreenCounter%=0
              ExitfcEdit%=%True END SELECT
     END SELECT
  LOOP
  END SUB
  SUB GetChar(ExitCode$,A$)
  A$=""
  DO WHILE LEN(A$)=0
     A$=INKEY$
  LOOP
  SELECT CASE LEN(A$)
     CASE 1
        I%= ASC(A$)
        SELECT CASE I%
           CASE 27
              ExitCode$="ESC"
```

```
              CASE 13
                 ExitCode$="CR"
              CASE 9
                 ExitCode$="TAB"
              CASE 8
                 ExitCode$="BACK"
              CASE 48 TO 57
                 ExitCode$="DIGIT"

CASE ELSE
                 ExitCode$="CHAR"
           END SELECT
        CASE 2
           A$=RIGHT$(A$,1) : I%= ASC(A$)
           SELECT CASE I%
              CASE 71
                 ExitCode$="HOME"
              CASE 72
                 ExitCode$="UP"
              CASE 73
                 ExitCode$="PG UP"
              CASE 75
                 ExitCode$="LEFT"
              CASE 77
                 ExitCode$="RIGHT"
              CASE 79
                 ExitCode$="END"
              CASE 80
                 ExitCode$="DOWN"
              CASE 81
                 ExitCode$="PG DN"
              CASE 82
                 ExitCode$="INS"
              CASE 83
                 ExitCode$="DEL"
              CASE 59
                 ExitCode$="F1"
              CASE 60
                 ExitCode$="F2"
              CASE 61
                 ExitCode$="F3"
              CASE 62
                 ExitCode$="F4"
              CASE 63
                 ExitCode$="F5"
              CASE 64
                 ExitCode$="F6"
              CASE 65
                 ExitCode$="F7"
              CASE 66
                 ExitCode$="F8"
              CASE 67
                 ExitCode$="F9"
              CASE 68
                 ExitCode$="F10"
           END SELECT
        END SELECT
END SUB

'FILE : LIM_EDIT.BAS

SUB LimEdit(LimNr%,ScreenCounter%)'??? add arguments as required

SHARED LimitsName$(),LimitsDesc$(),LimitsAdap%()
SHARED LimitsMode%(),LimitsRate%(),LimitsStim%()
SHARED LimitsInt%(),LimitsTrig%(),LimitsSound%()
SHARED LimitsRand%(),TotalLimits%

Modality$(1)="CS"
Modality$(2)="WS"
Modality$(3)="CR"
Modality$(4)="HF"

TempName$=LimitsName$(LimNr%)
TempDesc$=LimitsDesc$(LimNr%)
TempAdap$=RIGHT$(STR$(LimitsAdap%(LimNr%)/10),4)
TempAdap$=STRING$(4-LEN(TempAdap$),32)+TempAdap$
FOR I%=1 TO 6
```

```
    TempMode%(I%)=LimitsMode%(LimNr%,I%)
    TempRate$(I%)=RIGHT$(STR$(LimitsRate%(LimNr%,I%)/10),4)
    TempRate$(I%)=STRING$(4-LEN(TempRate$(I%)),32)+TempRate$(I%)
    TempStim$(I%)=RIGHT$(STR$(LimitsStim%(LimNr%,I%)),1)
    TempInt$(I%)=RIGHT$(STR$(LimitsInt%(LimNr%,I%)),2)
    IF LEN(TempInt$(I%))=1 THEN TempInt$(I%)=" "+TempInt$(I%)
    IF LimitsTrig%(LimNr%,I%)=%False THEN
      TempTrig$(I%)=" NO"
    ELSE
      TempTrig$(I%)="YES"
    END IF
    IF LimitsSound%(LimNr%,I%)=%False THEN
      TempSound$(I%)=" NO"
    ELSE
      TempSound$(I%)="YES"
    END IF
    IF LimitsRand%(LimNr%,I%)=%False THEN
      TempRand$(I%)=" NO"
    ELSE
      TempRand$(I%)="YES"
    END IF
  NEXT I%
  LOCATE 3,3:PRINT "NAME:"
  LOCATE 4,3:PRINT "DESCR:"
  LOCATE 6,3:PRINT "ADAPTATION TEMP:"
  LOCATE 8,3:PRINT "SEQUENCE Nr:"
  LOCATE 9,3:PRINT "MODALITY:"
  LOCATE 10,3:PRINT "TEMP RATE(deg/sec):"
  LOCATE 11,3:PRINT "No OF STIMULI:"
  LOCATE 12,3:PRINT "INTERVAL (sec):"
  LOCATE 13,3:PRINT "MAN. TRIG. OPTION:"
  LOCATE 14,3:PRINT "SOUND OPTION:"
  LOCATE 15,3:PRINT "RANDOMIZE WITH NEXT:"
  FOR I%=1 TO 6
    LOCATE 8,14+10*I%:PRINT "-";I%;"-"
  NEXT I%
  LOCATE 18,3:PRINT "SAVE PROGRAM"
  LOCATE 19,3:PRINT "RETURN TO LIMITS TESTS LIST (ABANDON PROGRAM)"
  LOCATE 20,3:PRINT "RETURN TO MAIN MENU (ABANDON PROGRAM)"
  LOCATE 3,10 :PRINT TempName$
  LOCATE 4,10:PRINT TempDesc$
  LOCATE 6,20:PRINT USING "\    \":TempAdap$
  FOR I%=1 TO 6
    LOCATE 9,16+10*I%
    IF TempMode%(I%)<>0 THEN Print Modality$(TempMode%(I%))
    LOCATE 10,14+10*I%:PRINT USING "\  \";TempRate$(I%)
    LOCATE 11,17+10*I%:PRINT TempStim$(I%)
    LOCATE 12,16+10*I%:PRINT USING "\\";TempInt$(I%)
    LOCATE 13,15+10*I%:PRINT TempTrig$(I%)
    LOCATE 14,15+10*I%:PRINT TempSound$(I%)
    LOCATE 15,15+10*I%:PRINT TempRand$(I%)
  NEXT I%
  Sequence%=1
  InputField%=1
  ExitLimEdit%=%False
  DO UNTIL ExitLimEdit%
    SELECT CASE InputField%
      CASE 1 'NAME
        CALL Instruction(1,"input or modify test name")
        CALL EngEdit(3,10,20,TempName$,ExitCode$)
      CASE 2 'description
        CALL Instruction(1,"input or modify test description")
        CALL EngEdit(4,10,40,TempDesc$,ExitCode$)
      CASE 3 'temp
        CALL Instruction(1,"input or modify adaptation temperature")
        CALL DecEdit(6,20,4,TempAdap$,ExitCode$)
      CASE 4 '
        CALL Instruction(1,"toggle modalities using TAB key")
        I%=Sequence%
        LOCATE 9,16+10*Sequence%:COLOR 0,7
        IF TempMode%(I%)<>0 THEN Print Modality$(TempMode%(I%)) ELSE PRINT "  "
        CALL GetChar(ExitCode$,A$)
        IF ExitCode$="TAB" THEN INCR TempMode%(I%)
        IF TempMode%(I%)>4 THEN TempMode%(I%)=1
        LOCATE 9,16+10*Sequence%:COLOR 7,0
        IF TempMode%(I%)<>0 THEN Print Modality$(TempMode%(I%)) ELSE PRINT "  "
      CASE 5 '
        CALL Instruction(1,"input or modify temperature rate")
```

```
    CALL DecEdit(10,14+10*Sequence%,4,TempRate$(Sequence%),ExitCode$)
  CASE 6 '
    CALL Instruction(1,"input or modify number of stimuli")
    CALL NatEdit(11,17+10*Sequence%,1,TempStim$(Sequence%),ExitCode$)
  CASE 7
    CALL Instruction(1,"input or modify time imterval")
    CALL NatEdit(12,16+10*Sequence%,2,TempInt$(Sequence%),ExitCode$)
  CASE 8 '
    CALL Instruction(1,"toggle YES/NO using TAB key")
    CALL BinEdit(13,15+10*Sequence%,"YES"," NO",TempTrig$(Sequence%),ExitCode$)
  CASE 9 '
    CALL Instruction(1,"toggle YES/NO using TAB key")
    CALL BinEdit(14,15+10*Sequence%,"YES"," NO",TempSound$(Sequence%),ExitCode$)
  CASE 10'
    CALL Instruction(1,"toggle YES/NO using TAB key")
    CALL BinEdit(15,15+10*Sequence%,"YES"," NO",TempRand$(Sequence%),ExitCode$)
  CASE 11 'save
    CALL Instruction(1,"")
    COLOR 0,7
    LOCATE 18,3:PRINT "SAVE PROGRAM"
    CALL GetChar(ExitCode$,A$)
    COLOR 7,0
    LOCATE 18,3:PRINT "SAVE PROGRAM"
  CASE 12'return to limits menu
    CALL Instruction(1,"")
    COLOR 0,7
    LOCATE 19,3:PRINT "RETURN TO LIMITS TESTS LIST (ABANDON PROGRAM)"
    CALL GetChar(ExitCode$,A$)
    COLOR 7,0
    LOCATE 19,3:PRINT "RETURN TO LIMITS TESTS LIST (ABANDON PROGRAM)"
  CASE 13'return to main menu
    CALL Instruction(1,"")
    COLOR 0,7
    LOCATE 20,3:PRINT "RETURN TO MAIN MENU (ABANDON PROGRAM)"
    CALL GetChar(ExitCode$,A$)
    COLOR 7,0
    LOCATE 20,3:PRINT "RETURN TO MAIN MENU (ABANDON PROGRAM)"
END SELECT CALL Instruction(2,"")
SELECT CASE ExitCode$
  CASE "UP"
    SELECT CASE InputField%
      CASE 2,3,4,5,6,7,8,9,10,11,12,13
        DECR InputField%
    END SELECT
  CASE "DOWN"
    SELECT CASE InputField%
      CASE 1,2,3,4,5,6,7,8,9,10,11,12
        INCR InputField%
    END SELECT
  CASE "LEFT"
    SELECT CASE InputField%
      CASE 2
        DECR InputField%
      CASE 4 TO 10
        IF Sequence%>1 THEN DECR Sequence%
    END SELECT
  CASE "RIGHT"
    SELECT CASE InputField%
      CASE 1
        INCR InputField%
      CASE 4 TO 10
        IF Sequence%<6 THEN INCR Sequence%
    END SELECT
  CASE "CR"
    SELECT CASE InputField%
      CASE 1,2,3,4,5,6,7
        INCR InputField%
      CASE 11 'SAVE 'TEST DATA
        DataTested%=%True
        IF TempName$ ="" OR TempName$ = STRING$(20,32) THEN
          DataTested%=%False:InputField%=1
          CALL Instruction(2,"to save test name must be defined")
```

```
     END IF
     IF VAL(TempAdap$)>35 OR VAL(TempAdap$)<25 THEN
        DataTested%=%False:InputField%=3
        CALL Instruction(2,"adaptation temperature must be between 25 and 35 c
     END IF
     FOR I%=1 TO 6
        IF VAL(TempStim$(I%))>0 THEN
           IF TempMode%(I%)=0 THEN
              DataTested%=%False:InputField%=4:Sequence%=I%
              CALL Instruction(2,"modality must be defined")
           END IF
           IF VAL(TempRate$(I%))=0 THEN
              DataTested%=%False:InputField%=5:Sequence%=I%
              CALL Instruction(2,"rate must be defined")
           END IF
           IF VAL(TempInt$(I%))=0 THEN
              DataTested%=%False:InputField%=7:Sequence%=I%
              CALL Instruction(2,"interval must be defined")
           END IF
           FOR J% =1 TO I%-1
           IF VAL(TempStim$(J%))=0 THEN
              DataTested%=%False:InputField%=6:Sequence%=J%
              CALL Instruction(2,"nr of stimuli must be defined")
           END IF
           NEXT J%
        END IF
     NEXT I%
     IF DataTested%=%True THEN
        DataTested%=%False:InputField%=6:Sequence%=1
        FOR I%=1 TO 6
           IF VAL(TempStim$(I%))>0 THEN DataTested%=%True
        NEXT I%
     END IF
'*********

IF DataTested%=%True THEN
        LimitsName$(LimNr%)=TempName$
        LimitsDesc$(LimNr%)=TempDesc$
        LimitsAdap%(LimNr%)=VAL(TempAdap$)*10
        FOR I%=1 TO 6
        LimitsMode%(LimNr%,I%)=TempMode%(I%)
        LimitsRate%(LimNr%,I%)=VAL(TempRate$(I%))*10
        LimitsStim%(LimNr%,I%)=VAL(TempStim$(I%))
        LimitsInt%(LimNr%,I%)=VAL(TempInt$(I%))
        IF TempTrig$(I%)=" NO" THEN
           LimitsTrig%(LimNr%,I%)=%False
        ELSE
           LimitsTrig%(LimNr%,I%)=%True
        END IF
        IF TempSound$(I%)=" NO" THEN
           LimitsSound%(LimNr%,I%)=%False
        ELSE
           LimitsSound%(LimNr%,I%)=%True
        END IF
        IF TempRand$(I%)=" NO" THEN
           LimitsRand%(LimNr%,I%)=%False
        ELSE
           LimitsRand%(LimNr%,I%)=%True
        END IF
     NEXT I%
     IF LimNr%>TotalLimits% THEN INCR TotalLimits%
     OPEN "LIMITS.TSA" FOR OUTPUT AS #1
     WRITE #1 ,TotalLimits%
     FOR I%=1 TO TotalLimits%
        WRITE #1, LimitsName$(I%),LimitsDesc$(I%),LimitsAdap%(I%)
        FOR J% =1 TO 6
           WRITE #1,LimitsMode%(I%,J%),LimitsRate%(I%,J%),LimitsStim%(I%,J%
           WRITE #1,LimitsInt%(I%,J%),LimitsTrig%(I%,J%),LimitsSound%(I%,J%
           WRITE #1,LimitsRand%(I%,J%)
        NEXT J%
     NEXT I%
     CLOSE #1
     ScreenCounter%=0
     ExitLimEdit%=%True
```

```
        END IF
      CASE 12' return to limits
        DECR ScreenCounter%
        ExitLimEdit%=%True
      CASE 13
        ScreenCounter%=0
        ExitLimEdit%=%True END SELECT
  END SELECT
LOOP
END SUB
'FILE :LIM_PRT.BAS
SUB LimitsPrint
SHARED LimitsName$(),LimitsAdap%(),LimitsMode%(),LimitsRate%()
SHARED TestCode%,Header$
SHARED LimResults%(),TestSequence%()
SHARED ID$,Patient$
'LPRINT CHR$(15)
LPRINT "I.D. NUMBER:"
LPRINT ID$
LPRINT
LPRINT "NAME:"
LPRINT Patient$
LPRINT
LPRINT "DATE:";DATE$
LPRINT
LPRINT "METHOD : L   TS"
LPRINT "TEST NAME:"
LPRINT LimitsName$(TestCode%)
LPRINT
LPRINT "ADAPTATION TEMP:";
LPRINT USING "##.#";LimitsAdap%(TestCode%)/10
LPRINT
LPRINT "MODAL.   RATE    RESULT"
FOR I%=1 TO 36
  IF TestSequence%(I%)>0 THEN
    SELECT CASE LimitsMode%(TestCode%,TestSequence%(I%))
      CASE 1
        LPRINT " CS    ";
      CASE 2
        LPRINT " HS    ";
      CASE 3
        LPRINT " CP    ";
      CASE 4
        LPRINT " HP    ";
    END SELECT
    LPRINT USING "##.#";LimitsRate%(TestCode%,TestSequence%(I%))/10;
    LPRINT SPC(4);
    LPRINT USING "##.#";LimResults%(I%)/10
  END IF
  NEXT I%
  LPRINT CHR$(12)
END SUB SUB NatEdit(R%,C%,L%,S$,E$)
LOCATE R%,C% : COLOR 0,7 :IF S$="" THEN S$=STRING$(L%,32)
PRINT S$
ExitNatEdit%=%False
DO UNTIL ExitNatEdit%
  LOCATE R%,C%+L%-1
  CALL GetChar(E$,A$)
  SELECT CASE E$
    CASE "DIGIT"
      S$=S$+A$
      IF LEN(S$)>L% THEN S$=RIGHT$(S$,L%)
      LOCATE R%,C% : PRINT S$
    CASE "DEL"
      S$=STRING$(L%,32)
      LOCATE R%,C% : PRINT S$
    CASE "UP","DOWN","CR","ESC","LEFT","RIGHT","INS"
      ExitNatEdit%=%True
  END SELECT
LOOP
LOCATE R%,C% :COLOR 7,0 : PRINT S$
END SUB
```

```
SUB FindPatient(Count%,C%,SearchID$)
SHARED Index&(),TotalPatients%

CALL Instruction(1,"INPUT PATIENTS ID NUMBER USING NUMERIC KEYS")
CALL Instruction(2,"ERASE THE NUMBER USING <DEL> KEY")
LOCATE 3,8:PRINT "PATIENT ID NUMBER:"
LOCATE 18,8:PRINT "RETURN TO MAIN MENU"
InputField%=1
ExitFindPat%=%False DO UNTIL ExitFindPat%
   LOCATE 3,26:PRINT SearchID$
   LOCATE 18,8:PRINT "RETURN TO MAIN MENU"

SELECT CASE InputField%
     CASE 1 'ID
       CALL Natedit(3,26,9,SearchID$,ExitCode$)
       SELECT CASE ExitCode$
         CASE "CR"
           IF VAL(SearchID$) > 0 THEN
             Found%=%False
             Count%=1
               DO UNTIL Found%=%True OR Count%>TotalPatients%
                 IF VAL(SearchID$)=Index&(Count%) THEN
                   Found%=%True
                 ELSE
                   INCR Count%
                 END IF
               LOOP
             ExitFindPat%=%True:INCR C%
           END IF
         CASE "DOWN"
           InputField%=2
       END SELECT
     CASE 2 ' RETURN
       COLOR 0,7
       LOCATE 18,8:PRINT "RETURN TO MAIN MENU"
       CALL GetChar(ExitCode$,A$)
       COLOR 7,0
       SELECT CASE ExitCode$
         CASE "CR"
           C%=0 : ExitFindPat%=%True
         CASE "UP"
           InputField%=1
       END SELECT
   END SELECT
LOOP
END SUB

'***************************************************************

SUB PatientEdit(I%,C%,SearchID$)
SHARED Index&(),TotalPatients%
SHARED ID$,Patient$,Birth$,Year$,Code$,Sex$,Diabets$,Uremia$,Drugtox$,FamNP$
SHARED Date1$,Date2$,Date3$,D1$,D2$,D3$
SHARED RecID$,RecPatient$,RecBirth$,RecCode$,RecD1$,RecD2$,RecD3$ OPEN "R",#1,"PATIENTS.TSA",34
FIELD #1,4 AS RecID$,_
         20 AS RecPatient$,_
          2 AS RecBirth$,_
          2 AS RecCode$ ,_
          2 AS RecD1$,_
          2 AS RecD2$,_
          2 AS RecD3$ LOCATE 3,8:PRINT "PATIENT ID NUMBER:"
   LOCATE 3,50:PRINT "LAST 3 TESTS DATES:"
   LOCATE 5,8:PRINT "PATIENT NAME:"
   LOCATE 7,8:PRINT "YEAR OF BIRTH:"
   LOCATE 9,8:PRINT "SEX:"
   LOCATE 11,35:PRINT "DISEASES:"
   LOCATE 13,8:PRINT "DIABETES:"              ' prepare screen
   LOCATE 13,30:PRINT "UREMIA:"
   LOCATE 13,52:PRINT "DRUG TOXITICITY"
```

```
LOCATE 15,8:PRINT "FAMILIAL NF:"
LOCATE 15,30:PRINT "RESERVED:"
LOCATE 15,52:PRINT "RESERVED"

IF I%>TotalPatients% THEN
   TempID$=SearchID$
   TempName$=STRING$(20,32)
   TempYear$=STRING$(4,32)
   TempSex$=STRING$(6,32)
   TempDiabets$="   "
   TempUremia$="   "
   TempDrugtox$="   "
   TempFamNF$="   "
   TempDate1$=STRING$(10,32)
   TempDate2$=STRING$(10,32)
   TempDate3$=STRING$(10,32)
   InputField%=2
ELSE
   CALL GetPatient(I%)
   TempID$=ID$
   TempName$=Patient$
   TempYear$=Year$
   TempSex$=Sex$
   TempDiabets$=Diabets$
   TempUremia$=Uremia$
   TempDrugtox$=Drugtox$
   TempFamNF$=FamNF$
   TempDate1$=Date1$
   TempDate2$=Date2$
   TempDate3$=Date3$
   InputField%=12
END IF ExitPatEdit%=%False
DO UNTIL ExitPatEdit%
   CALL Instruction(1,"")
   CALL Instruction(2,"")
   LOCATE 3,26:PRINT TempID$
   LOCATE 5,26:PRINT TempName$
   LOCATE 7,26:PRINT TempYear$
   LOCATE 9,26:PRINT TempSex$
   LOCATE 13,24:PRINT TempDiabets$
   LOCATE 13,46:PRINT TempUremia$          ' display patient data
   LOCATE 13,68:PRINT TempDrugtox$
   LOCATE 15,24:PRINT TempFamNF$
   LOCATE 5,55:PRINT TempDate1$
   LOCATE 7,55:PRINT TempDate2$
   LOCATE 9,55:PRINT TempDate3$
   LOCATE 18,8:PRINT "RETURN TO MAIN MENU"
   LOCATE 20,8:PRINT "CONTINUE"
SELECT CASE InputField%
   CASE 1 'ID
      CALL Instruction(2,"REINPUT PATIENTS ID NUMBER USING NUMERIC KEYS")
      CALL Instruction(1,"ERASE THE NUMBER USING <DEL> KEY")
      CALL NatEdit(3,26,9,TempID$,ExitCode$)
   CASE 2 'NAME
      CALL ENGEDIT(5,26,20,TempName$,ExitCode$)
   CASE 3 'YEAR
      CALL Instruction(1,"INPUT PATIENTS BIRTH YEAR USING NUMERIC KEYS")
      CALL Instruction(1,"ERASE THE NUMBER USING <DEL> KEY")
      CALL NatEdit(7,26,4,TempYear$,ExitCode$)
   CASE 4 'SEX
      CALL Instruction(1,"TOGGLE MALE\FEMALE USING <TAB> KEY")
      CALL BinEdit(9,26,"MALE  ","FEMALE",TempSex$,ExitCode$)
   CASE 5 'DIABETS
      CALL Instruction(1,"TOGGLE YES\NO USING <TAB> KEY")
      CALL BinEdit(13,24,"YES","NO ",TempDiabets$,ExitCode$)
   CASE 6 'UREMIA
      CALL Instruction(1,"TOGGLE YES\NO USING <TAB> KEY")
      CALL BinEdit(13,46,"YES","NO ",TempUremia$,ExitCode$)
   CASE 7 'DRUGTOX
      CALL Instruction(1,"TOGGLE YES\NO USING <TAB> KEY")
      CALL BinEdit(13,68,"YES","NO ",TempDrugtox$,ExitCode$)
   CASE 8 'FAM
      CALL Instruction(1,"TOGGLE YES\NO USING <TAB> KEY")
      CALL BinEdit(15,24,"YES","NO ",TempFamNF$,ExitCode$)
```

```
    CASE 11 'RETURN
       COLOR 0,7
       LOCATE 18,8:PRINT "RETURN TO MAIN MENU"
       CALL Instruction(1,"This option does NOT save\update patient's data")
       CALL GetChar(ExitCode$,A$)
       COLOR 7,0
    CASE 12 'CONTINUE
       COLOR 0,7
       LOCATE 20,8:PRINT "CONTINUE"
       CALL Instruction(1,"This option   saves\updates patient's data")
       CALL GetChar(ExitCode$,A$)
       COLOR 7,0
END SELECT
SELECT CASE ExitCode$
   CASE "UP"
      SELECT CASE InputField%
         CASE 2,3,4,5,12
            DECR InputField%
         CASE 6,7
            InputField%=4
         CASE 8,11
            InputField%=InputField%-3
      END SELECT
   CASE "DOWN"
      SELECT CASE InputField%
         CASE 1,2,3,4,11
            INCR InputField%
         CASE 5,8
            InputField%=InputField%+3
      END SELECT
   CASE "LEFT"
      SELECT CASE InputField%
         CASE 6,7
            DECR InputField%
      END SELECT
   CASE "RIGHT"
      SELECT CASE InputField%
         CASE 5,6
            INCR InputField%
      END SELECT
   CASE "CR"
      SELECT CASE InputField%
         CASE 1 TO 10
            INCR InputField%
         CASE 11
            C%=0
            ExitPatEdit%=%True
         CASE 12
            IF I%>TotalPatients% THEN INCR TotalPatients%
            SaveFlag%=%False
            IF   TempID$<>ID$ THEN SaveFlag%=%True
            IF   TempName$<>Patient$ THEN SaveFlag%=%True
            IF   TempYear$<>Year$ THEN SaveFlag%=%True
            IF   TempSex$<>Sex$ THEN SaveFlag%=%True
            IF   TempDiabets$<>Diabets$ THEN SaveFlag%=%True
            IF   TempUremia$<>Uremia$ THEN SaveFlag%=%True
            IF   TempDrugtox$<>Drugtox$ THEN SaveFlag%=%True
            IF   TempFamNP$<>FamNP$ THEN SaveFlag%=%True
            IF SaveFlag%=%True THEN
               ID$=TempID$
               Patient$=TempName$
               Year$=TempYear$
               Sex$=TempSex$
               Diabets$=TempDiabets$
               Uremia$=TempUremia$
               Drugtox$=TempDrugtox$
               FamNP$=TempFamNP$
               Index&(I%)=VAL(ID$)
               CALL SavePatient(I%)
            END IF
            INCR C%
            ExitPatEdit%=%True
      END SELECT
  END SELECT
LOOP
CLOSE #1
END SUB
'**********************************************************
```

```
SUB GetPatient(N%)
SHARED ID$,Patient$,Birth$,Year$,Code$,Sex$,Diabets$,Uremia$,Drugtox$,FamNP$
SHARED Date1$,Date2$,Date3$,D1$,D2$,D3$
SHARED RecID$,RecPatient$,RecBirth$,RecCode$,RecD1$,RecD2$,RecD3$ GET #1,N%         'READ DATA FROM DISK
ID$=STR$(CVL(RecID$))
Patient$=RecPatient$
Year$=STR$(CVI(RecBirth$))

Code%=CVI(RecCode$)
IF (Code% AND 128) = 0 THEN Sex$="FEMALE" ELSE Sex$="MALE   "
IF (Code% AND  32) = 0 THEN Diabets$="NO " ELSE Diabets$="YES"
IF (Code% AND  16) = 0 THEN Uremia$="NO " ELSE Uremia$="YES"
IF (Code% AND   8) = 0 THEN Drugtox$="NO " ELSE Drugtox$="YES"
IF (Code% AND   4) = 0 THEN FamNP$="NO " ELSE FamNP$="YES"

I%=CVI(RecD1$)
IF I%=0  THEN
  Date1$=STRING$(10,32)
 ELSE
  DD%=I% MOD 40:I%=I%-DD% :MM%= I% MOD 12 :YY%=I%-MM%
  Date1$=STR$(MM%)+"-"+STR$(DD%)+"-"+STR$(1990+YY%)
END IF I%=CVI(RecD2$)
IF I%=0  THEN
  Date2$=STRING$(10,32)
 ELSE
  DD%=I% MOD 40:I%=I%-DD% :MM%= I% MOD 12 :YY%=I%-MM%
  Date2$=STR$(MM%)+"-"+STR$(DD%)+"-"+STR$(1990+YY%)
END IF I%=CVI(RecD3$)
IF I%=0  THEN
  Date3$=STRING$(10,32)
 ELSE
  DD%=I% MOD 40:I%=I%-DD% :MM%= I% MOD 12 :YY%=I%-MM%
  Date3$=STR$(MM%)+"-"+STR$(DD%)+"-"+STR$(1990+YY%)
END IF

END SUB

SUB SavePatient(N%)
SHARED ID$,Patient$,Birth$,Year$,Code$,Sex$,Diabets$,Uremia$,Drugtox$,FamNP$
SHARED Date1$,Date2$,Date3$,D1$,D2$,D3$
SHARED RecID$,RecPatient$,RecBirth$,RecCode$,RecD1$,RecD2$,RecD3$ Code%=0
IF Sex$="MALE   " THEN Code%=Code%+128
IF Diabets$="YES" THEN Code%=Code%+32
IF Uremia$="YES" THEN Code%=Code%+16
IF Drugtox$="YES" THEN Code%=Code%+8
IF FamNP$="YES" THEN Code%=Code%+4
Code$=MKI$(Code%)
IF VAL(Date1$)<>0 THEN
  MM%=VAL(LEFT$(Date1$,2))
  DD%=VAL(MID$(Date1$,4,2))
  YY%=VAL(RIGHT$(Date1$,4))-1990
  I%=480*YY%+40*MM%+DD%
  D1$=MKI$(I%)
 ELSE
  D1$=MKI$(0)
END IF IF VAL(Date2$)<>0 THEN
  MM%=VAL(LEFT$(Date2$,2))
  DD%=VAL(MID$(Date2$,4,2))
  YY%=VAL(RIGHT$(Date2$,4))-1990
  I%=480*YY%+40*MM%+DD%
  D2$=MKI$(I%)
 ELSE
  D2$=MKI$(0)
END IF
```

```
IF VAL(Date3$)<>0 THEN
  MM%=VAL(LEFT$(Date3$,2))
  DD%=VAL(MID$(Date3$,4,2))
  YY%=VAL(RIGHT$(Date3$,4))-1990
  I%=480*YY%+40*MM%+DD%
  D3$=MKI$(I%)
ELSE
  D3$=MKI$(0)
END IF
LSET RecID$=MKL$(VAL(ID$))
LSET RecPatient$=Patient$
LSET RecBirths=MKI$(VAL(Year$))
LSET RecCode$=Code$
LSET RecD1$=D1$
LSET RecD2$=D2$
LSET RecD3$=D3$

PUT #1,N%

END SUB

SUB BinEdit(R%,C%,T$,F$,S$,E$)
COLOR 0,7
ExitBinEdit%=%False
DO UNTIL ExitBinEdit%
    LOCATE R%,C% :PRINT S$
   CALL GetChar(E$,A$)
   SELECT CASE E$
      CASE "CR","UP","DOWN","LEFT","RIGHT"
         ExitBinEdit%=%True
      CASE "TAB"
         IF S$=T$ THEN S$=F$ ELSE S$=T$
   END SELECT
LOOP
LOCATE R%,C% :COLOR 7,0 : PRINT S$
END SUB SUB RunLimits SHARED LimitsName$(),LimitsDesc$(),LimitsAdap%(),LimitsMode%(),LimitsRate%()
SHARED LimitsInt%(),LimitsTrig%(),LimitsSound%(),LimitsStim%(),LimitsRand%()
SHARED TestCode%,Header$,ScreenCounter%
SHARED LimResults%(),TestSequence%()
SHARED StopStimulus%
SHARED Tout!()
SHARED Tin,FilteredTemp
'SET TEST PARAMETERS
Counter%=1:RandomFlag%=%False:FirstRandom%=0:LastRandom%=0
FOR I% = 1 TO 6
   IF LimitsRand%(TestCode%,I%)=%True AND RandomFlag%=%False THEN
      FirstRandom%=Counter%:RandomFlag%=%True
   END IF
   FOR J% = 1 TO LimitsStim%(TestCode%,I%)
      TestSequence%(Counter%)=I%
      INCR Counter%
   NEXT J%
   IF LimitsRand%(TestCode%,I%)=%False AND RandomFlag%=%True THEN
      LastRandom%=Counter%-1:RandomFlag%=%False
   END IF
   IF RandomFlag%=%False   THEN
      IF FirstRandom%<>0 THEN
         FOR J%=FirstRandom% TO LastRandom%-1
            K%=INT(RND*(LastRandom%-J%+1))+J%
            SWAP TestSequence%(J%),TestSequence%(K%)
         NEXT J%
         FirstRandom%=0
      END IF
      FOR J%=Counter% TO 6*I%
         TestSequence%(J%)=0
```

```
      INCR Counter%
    NEXT J%
  END IF
NEXT I%

INCR ScreenCounter%
Adapt%=LimitsAdap%(TestCode%)

'SET SCREEN
LOCATE 1,3:PRINT "TEST NAME:"
LOCATE 1,15:PRINT LimitsName$(TestCode%)
LOCATE 2,1:PRINT "50"
LOCATE 15,1:PRINT" 0"
LOCATE 14-Adapt%\42,1:PRINT USING "##.#";Adapt%/10
VIEW (36,12)-(628,112),,1
WINDOW (0,0)-(37,500)
LINE (0,Adapt%)-(37,Adapt%)
'SET SYMBOLIC GRAPH
FOR I% = 1 TO 36
  SELECT CASE LimitsMode%(TestCode%,TestSequence%(I%))
    CASE 1 ' CS
      LINE (I%-0.1,Adapt%)-(I%-0.1,Adapt%-20)
      LINE (I%+0.1,Adapt%)-(I%+0.1,Adapt%-20)
    CASE 2 ' HS
      LINE (I%-0.1,Adapt%)-(I%-0.1,Adapt%+20)
      LINE (I%+0.1,Adapt%)-(I%+0.1,Adapt%+20)
    CASE 3 ' LF
      LINE (I%-0.1,Adapt%)-(I%-0.1,Adapt%-100)
      LINE (I%+0.1,Adapt%)-(I%+0.1,Adapt%-100)
    CASE 4 ' HF
      LINE (I%-0.1,Adapt%)-(I%-0.1,Adapt%+100)
      LINE (I%+0.1,Adapt%)-(I%+0.1,Adapt%+100)
  END SELECT
  LimResults%(I%)=0
NEXT I%

TerminateTest%=%False
LimitsCursor%=1
DO UNTIL TerminateTest%
  CALL Instruction(2,"========= MOVE CURSOR TO CONTINUATION POINT =========")
  CALL Instruction(3,"TOUCH SPACEBAR TO START.PRESS ESC TO TERMINATE TEST")

LOCATE 16,5+2*LimitsCursor%:PRINT"|"
  CALL GetChar(ExitCode$,A$)
  LOCATE 16,5+2*LimitsCursor%:PRINT" "
  SELECT CASE ExitCode$
   CASE "CHAR"
    IF ASC(A$)=32 THEN
      TIMER OFF
      CALL Instruction(2,"========= TO PAUSE TEST - PRESS  S =========")
      CALL Instruction(3,"")

StopRun%=%False
      DO UNTIL StopRun%
        Tin=Adapt%/10
        LOCATE 16,5+2*LimitsCursor%:PRINT"|"
        IF TestSequence%(LimitsCursor%)<>0 THEN
          Delta=0.001*LimitsRate%(TestCode%,TestSequence%(LimitsCursor%))
          Prediction=0.05*LimitsRate%(TestCode%,TestSequence%(LimitsCursor%))
          IF LimitsMode%(TestCode%,TestSequence%(LimitsCursor%)) MOD 2<>0 THEN
            Delta=-Delta :Prediction=-Prediction
          END IF
          R%=17+((LimitsCursor%-1) MOD 6)
          C%=2*LimitsCursor%+4
          'WAIT FOR INTERVAL TO EXPIRE
          StartInterval=TIMER:EndInterval%=%False
          CALL Instruction(3,"WAITING INTERVAL                     ")
          Count%=0
          DO UNTIL EndInterval%
            INCR Count%
            A$=INKEY$
            IF UCASE$(A$)="S"THEN EndInterval%=%True:StopRun%=%True
            Interval=LimitsInt%(TestCode%,TestSequence%(LimitsCursor%))
            TimeToGo=Interval+StartInterval-TIMER
            IF Count%=50 THEN
              Count%=0
```

```
            LOCATE 24,40:PRINT USING "##.#";TimeToGo;
          END IF
          CALL ContLoop
          IF TimeToGo<=0 THEN EndInterval%=%True
        LOOP 'wait for trigger
        IF LimitsTrig%(TestCode%,TestSequence%(LimitsCursor%))=%False THEN
          Trigger%=%False
          CALL Instruction(3,"PRESS SPACEBAR TO TRIGGER STIMULUS")
          DO UNTIL Trigger%
            A$=INKEY$
            IF UCASE$(A$)="S" THEN
              Trigger%=%True:StopRun%=%True
            END IF
            IF A$=" " THEN Trigger%=%True
            CALL ContLoop
          LOOP
        END IF 'APPLY STIMULUS
        I%=LimitsCursor%
        IF LimResults%(I%)=0 THEN
          SELECT CASE LimitsMode%(TestCode%,TestSequence%(I%))
            CASE 1 ' CS
              LINE (I%-0.1,Adapt%)-(I%-0.1,Adapt%-20),0
              LINE (I%+0.1,Adapt%)-(I%+0.1,Adapt%-20),0
            CASE 2 ' HS
              LINE (I%-0.1,Adapt%)-(I%-0.1,Adapt%+20),0
              LINE (I%+0.1,Adapt%)-(I%+0.1,Adapt%+20),0
            CASE 3 ' CP
              LINE (I%-0.1,Adapt%)-(I%-0.1,Adapt%-100),0
              LINE (I%+0.1,Adapt%)-(I%+0.1,Adapt%-100),0
            CASE 4 ' HP
              LINE (I%-0.1,Adapt%)-(I%-0.1,Adapt%+100),0
              LINE (I%+0.1,Adapt%)-(I%+0.1,Adapt%+100),0
          END SELECT
        ELSE
          LINE (I%,Adapt%)-(I%,LimResults%(I%)),0
        END IF
        LINE (I%,Adapt%)-(I%,Adapt%)
        IF LimitsSound%(TestCode%,TestSequence%(I%))<>0 THEN BEEP
        CALL Instruction(3,"STIMULUS IN PROCESS")
        StopStimulus%=StopRun%
        Count%=0

DO UNTIL StopStimulus%
          Tin=Tin+Delta
          CALL ContLoop
          INCR Count%
          IF Count%=50 THEN
            Count%=0
            LINE -(I%,(FilteredTemp+Prediction)*10)
            LOCATE R%,C%:PRINT USING "##.#";FilteredTemp+Prediction;
          END IF
          IF FilteredTemp>=50 THEN StopStimulus%=%True
          IF FilteredTemp<=0.5 THEN StopStimulus%=%True
          A$=INKEY$
          IF LEN(A$)>0 THEN StopStimulus%=%True
          IF UCASE$(A$)="S"THEN StopRun%=%True:StopStimulus%=%True
          KBRD%=INP(561)
          IF (KBRD% AND 1)=1 THEN  StopStimulus%=%True
          IF (KBRD% AND 2)=2 THEN  StopStimulus%=%True
        LOOP
        LOCATE R%,C%:PRINT USING "##.#";FilteredTemp+Prediction;
        LimResults%(LimitsCursor%)=INT((FilteredTemp+Prediction)*10)
      END IF LOCATE 16,5+2*LimitsCursor%:PRINT" "
      IF LimitsCursor%<36 THEN INCR LimitsCursor% ELSE StopRun%=%True
    LOOP
    TIMER ON
  END IF
CASE "LEFT"
  IF LimitsCursor% >1 THEN DECR LimitsCursor%
CASE "RIGHT"
  IF LimitsCursor% <36 THEN INCR LimitsCursor%
```

```
    CASE "ESC"
      TerminateTest%=%True
    END SELECT
LOOP

END SUB

SUB RunStairs

SHARED StairsName$(),StairsDesc$(),StairsAdap%(),StairsMode%(),StairsRate%()
SHARED StairsInt%(),StairsTrig%(),StairsSound%()
SHARED StairsFirst%(),StairsSecond%(),StairsThird%()
SHARED TestCode%,Header$,ScreenCounter%
SHARED StResults%()
SHARED StopStimulus%
SHARED Tout&()
SHARED Tin,FilteredTemp 'SET TEST PARAMETERS
INCR ScreenCounter%
Adapt%=StairsAdap%(TestCode%)
SearchMode$="COARSE":Answer%=%False
Tstop=Adapt%/10
FirstStep=StairsFirst%(TestCode%)/10
SecondStep=StairsSecond%(TestCode%)/10
ThirdStep=StairsThird%(TestCode%)/10
StairsCursor%=1
Delta=0.001*StairsRate%(TestCode%)
Prediction=0.05*StairsRate%(TestCode%)
IF StairsMode%(TestCode%) = 1 THEN
   Delta=-Delta :Prediction=-Prediction
   FirstStep=-FirstStep:SecondStep=-SecondStep:
   ThirdStep=-ThirdStep
END IF
SearchMode$="COARSE"
TotalFineAnswers%=0:FineNoAnswers%=0:FineSum=0

'SET SCREEN
LOCATE 1,3:PRINT "TEST NAME:"
LOCATE 1,15:PRINT StairsName$(TestCode%)
LOCATE 2,1:PRINT "50"
LOCATE 15,1:PRINT" 0"
LOCATE 14-Adapt%\42,1:PRINT USING "##.#";Adapt%/10
VIEW (36,12)-(628,112),,1
WINDOW (0,0)-(37,500)
LINE (0,Adapt%)-(37,Adapt%)

TerminateTest%=%False

DO UNTIL TerminateTest%
   CALL Instruction(2,"TOUCH SPACEBAR TO START.PRESS ESC TO TERMINATE TEST")
   CALL Instruction(3,"")
   LOCATE 16,5+2*StairsCursor%:PRINT"|"
   CALL GetChar(ExitCode$,A$)
   LOCATE 16,5+2*StairsCursor%:PRINT" "
   SELECT CASE ExitCode$
    CASE "CHAR"
     IF ASC(A$)=32 THEN
       TIMER OFF
       CALL Instruction(2,"========= TO PAUSE TEST - PRESS  S =========")
       CALL Instruction(3,"")
       StopRun%=%False DO UNTIL StopRun%
         Tin=Adapt%/10
         LOCATE 16,5+2*StairsCursor%:PRINT"|"
'WAIT FOR INTERVAL TO EXPIRE
StartInterval=TIMER:EndInterval%=%False
CALL Instruction(3,"WAITING INTERVAL
Count%=0

DO UNTIL EndInterval%
  INCR Count%
  A$=INKEY$
  IF UCASE$(A$)="S"THEN EndInterval%=%True:StopRun%=%True
  Interval=StairsInt%(TestCode%)
  TimeToGo=Interval+StartInterval-TIMER
  IF Count%=100 THEN
    Count%=0
```

```
      LOCATE 24,40:PRINT USING "##";TimeToGo;
   END IF
   CALL ContLoop
   IF TimeToGo<=0 THEN EndInterval%=%True
LOOP IF StairsTrig%(TestCode%)=%True THEN
   'WAIT FOR MANUAL TRIGGER
   Trigger%=%False
   CALL Instruction(3,"PRESS SPACEBAR TO TRIGGER STIMULUS")

DO UNTIL Trigger%
      CALL GetChar(ExitCode$,A$)
      IF ExitCode$="CHAR" AND ASC(A$)=32 THEN  Trigger%=%True
      IF ExitCode$="CHAR" AND UCASE$(A$)="S" THEN
        Trigger%=%True:StopRun%=%True
      END IF
      CALL ContLoop
   LOOP
END IF
R%=17+((StairsCursor%-1) MOD 6)
C%=2*StairsCursor%+4
StopStimulus%=StopRun%
IF StopStimulus%=%False THEN
   'SET SEARCHMODE
   IF SearchMode$="INTER" AND Answer%=%False THEN  SearchMode$="FINE"
   IF SearchMode$="COARSE" AND Answer%=%True THEN  SearchMode$="INTER"
   SELECT CASE SearchMode$
     CASE "COARSE"
       Increment=FirstStep
     CASE "INTER"
       Increment=SecondStep
     CASE "FINE"
       Increment=ThirdStep
   END SELECT
   IF Answer%=%True THEN
     Tstop=Tstop-Increment
   ELSE
     Tstop=Tstop+Increment
   END IF IF StairsSound%(TestCode%)=%True THEN BEEP
   CALL Instruction(3,"STIMULUS IN PROCESS")
   Count%=0
END IF 'APPLY STIMULUS
DO UNTIL StopStimulus%
   Tin=Tin+Delta
   CALL ContLoop
   INCR Count%
   IF Count%=50 THEN
      Count%=0
      LOCATE R%,C%:PRINT USING "##.#";FilteredTemp+Prediction;
   END IF
   IF FilteredTemp+Prediction>=50 THEN StopStimulus%=%True
   IF FilteredTemp+Prediction<=0.5 THEN StopStimulus%=%True
   SELECT CASE StairsMode%(TestCode%)
     CASE 1 'COLD SENS ? CHECK IN ST_EDIT
       IF FilteredTemp+Prediction<=Tstop THEN StopStimulus%=%True
     CASE 2
       IF FilteredTemp+Prediction>=Tstop THEN StopStimulus%=%True
   END SELECT
   A$=INKEY$
   IF UCASE$(A$)="S" THEN StopRun%=%True:StopStimulus%=%True
LOOP Tin=Adapt%/10
IF StopRun%=%False THEN
   LINE (StairsCursor%-.25,Tstop*10)-(StairsCursor%+.25,Tstop*10)
   LINE (StairsCursor%,Tstop*10-7)-(StairsCursor%,Tstop*10+7)
   LOCATE R%,C%:PRINT USING "##.#";FilteredTemp+Prediction;
   LOCATE 16,5+2*StairsCursor%:PRINT"?"
   A$=""
   CALL Instruction(3,"WAITNG FOR PATIENT'S RESPONSE OR Y/N KEY")
   DO UNTIL A$="Y" OR A$="N"
      'KBRD%=INP(561)
      'IF (KBRD% AND 1)=1 THEN A$="Y": Answer%=%True
```

```
         'IF (KBRD% AND 2)=2 THEN A$="N": Answer%=%False
         A$=INKEY$
         A$=UCASE$(A$)
         IF A$="S"   THEN
            StopRun%=%True
            CALL Instruction(3,"test will be paused after patient's response")
         END IF
         IF A$="Y"   THEN Answer%=%True
         IF A$="N"   THEN Answer%=%False
         CALL ContLoop
       LOOP
       LOCATE 16,5+2*StairsCursor%
       PRINT A$
       IF SearchMode$="FINE" THEN
          INCR TotalFineAnswers%:FineSum=FineSum +FilteredTemp+Prediction
          IF Answer%=%False THEN INCR FineNoAnswers%
       END IF
       IF StairsCursor%<36 AND FineNoAnswers%<4 THEN
          INCR StairsCursor%
         ELSE
          StopRun%=%True:TerminateTest%=%True
       END IF
      END IF
    LOOP
    TIMER ON
    IF TerminateTest%=%True THEN
       AverageStairs=FineSum/TotalFineAnswers%
       LOCATE 1,30:PRINT "AVERAGE = ";:PRINT USING "##.#";AverageStairs
       CALL Instruction(2,"PRESS ANY KEY TO TERMINATE TEST")
       CALL Instruction(3,"")
       CALL GetChar(A$,B$)
     END IF
   END IF
  CASE "ESC"
   TerminateTest%=%True
 END SELECT
LOOP

END SUB
'FILE: SEL_TEST.BAS

SUB SelTest(Total%,TestChoice%,ScreenCounter%)
SHARED TestName$(),TestDesc$()
LOCATE 2,10:PRINT "NAME":LOCATE 2,50:PRINT"DESCRIPTION"
LOCATE 19,5:PRINT "RETURN TO METHOD SELECTION"
LOCATE 20,5:PRINT "RETURN TO MAIN MENU"
FOR I%=1 TO Total%
   LOCATE I%+2,5:PRINT TestName$(I%)
   LOCATE I%+2,35:PRINT TestDesc$(I%)
NEXT I%

IF Total%>0 THEN
   TestChoice%=1
 ELSE
   TestChoice%=20
   CALL Instruction(1,"there are no tests defined for this method")
END IF
ChoiceDone%=%False
DO UNTIL ChoiceDone%
   COLOR 0,7
   SELECT CASE TestChoice%
     CASE <16
      LOCATE TestChoice%+2,5:PRINT TestName$(TestChoice%)
      LOCATE TestChoice%+2,35:PRINT TestDesc$(TestChoice%)
     CASE 19
      LOCATE 19,5:PRINT "RETURN TO METHOD SELECTION"
     CASE 20
      LOCATE 20,5:PRINT "RETURN TO MAIN MENU"
   END SELECT
   COLOR 7,0
   KeyCode$=""

DO UNTIL LEN(KeyCode$)<>0
       KeyCode$=INKEY$
   LOOP
   IF LEN(KeyCode$)=2 THEN
     KeyNumber%=ASC(RIGHT$(KeyCode$,1))
```

```
ELSE
   KeyNumber%=ASC(KeyCode$)
END IF
SELECT CASE TestChoice%
  CASE <16
    LOCATE TestChoice%+2,5:PRINT TestName$(TestChoice%)
    LOCATE TestChoice%+2,35:PRINT TestDesc$(TestChoice%)
  CASE 19
    LOCATE 19,5:PRINT "RETURN TO METHOD SELECTION"
  CASE 20
    LOCATE 20,5:PRINT "RETURN TO MAIN MENU"
END SELECT
SELECT CASE KeyNumber%
   CASE 48,72
      SELECT CASE TestChoice%
         CASE 2 TO Total%
            DECR TestChoice%
         CASE 19
            IF Total%>0 THEN TestChoice%=Total%
         CASE 20
            TestChoice%=19
      END SELECT
   CASE 49,60
      SELECT CASE TestChoice%
         CASE 1 TO Total%-1
            INCR TestChoice%
         CASE Total%
            TestChoice%=19
         CASE 19
            TestChoice%=20
      END SELECT
   CASE 13
      ChoiceDone%=%True
      SELECT CASE TestChoice%
         CASE <16
           INCR ScreenCounter%
         CASE 19
           DECR ScreenCounter%
         CASE 20
           ScreenCounter%=0
      END SELECT
  END SELECT
LOOP
END SUB

'FILE : ST_EDIT.BAS

SUB StEdit(StNr%,ScreenCounter%)

SHARED StairsName$(),StairsDesc$(),StairsAdap%()
SHARED StairsMode%(),StairsRate%(),StairsInt%()
SHARED StairsFirst%(),StairsSecond%(),StairsThird%()
SHARED StairsTrig%(),StairsSound%(),StairsCatch%()
SHARED TotalStairs%

Modality$(1)="CS"
Modality$(2)="WS"

TempName$=StairsName$(StNr%)
TempDesc$=StairsDesc$(StNr%)
TempAdap$=RIGHT$(STR$(StairsAdap%(StNr%)/10),4)
TempAdap$=STRING$(4-LEN(TempAdap$),32)+TempAdap$
TempMode%=StairsMode%(StNr%)
TempRate$=RIGHT$(STR$(StairsRate%(StNr%)/10),4)
TempRate$=STRING$(4-LEN(TempRate$),32)+TempRate$
TempInt$= RIGHT$(STR$(StairsInt%(StNr%)),2)
IF LEN (TempInt$)=1 THEN TempInt$= " "+TempInt$
TempFirst$= RIGHT$(STR$(StairsFirst%(StNr%)/10),4)
TempFirst$=STRING$(4-LEN(TempFirst$),32)+TempFirst$
TempSecond$= RIGHT$(STR$(StairsSecond%(StNr%)/10),4)
TempSecond$=STRING$(4-LEN(TempSecond$),32)+TempSecond$
TempThird$= RIGHT$(STR$(StairsThird%(StNr%)/10),4)
TempThird$=STRING$(4-LEN(TempThird$),32)+TempThird$
IF StairsTrig%(StNr%)=%False THEN
   TempTrig$=" NO"
 ELSE
   TempTrig$="YES"
```

```
END IF
IF StairsSound%(StNr%)=%False THEN
   TempSound$=" NO"
 ELSE
   TempSound$="YES"
END IF
IF StairsCatch%(StNr%)=%False THEN
   TempCatch$=" NO"
 ELSE
   TempCatch$="YES"
END IF
LOCATE 3,5:PRINT "NAME:":LOCATE 3,12     :PRINT TempName$
LOCATE 4,5:PRINT "DESCR:":LOCATE 4,12    :PRINT TempDesc$
LOCATE 7,5:PRINT "ADAPTATION TEMP:"      :LOCATE 7,32:PRINT TempAdap$
LOCATE 8,5:PRINT "MODALITY:"
LOCATE 8,34:IF TempMode%<>0 THEN Print Modality$(TempMode%)
LOCATE 9,5:PRINT "TEMP RATE(deg/sec):"   :LOCATE 9,32:PRINT TempRate$
LOCATE 10,5:PRINT "INTERVAL (sec):"      :LOCATE 10,34:PRINT TempInt$
LOCATE 11,5:PRINT "COARSE SEARCH STEP"   :LOCATE 11,32:PRINT TempFirst$
LOCATE 12,5:PRINT "INTERMEDIATE SEARCH STEP":LOCATE 12,32:PRINT TempSecond$
LOCATE 13,5:PRINT "FINE SEARCH STEP"     :LOCATE 13,32:PRINT TempThird$
LOCATE 14,5:PRINT "MAN. TRIG. OPTION:"   :LOCATE 14,33:PRINT TempTrig$
LOCATE 15,5:PRINT "SOUND OPTION:"        :LOCATE 15,33:PRINT TempSound$
LOCATE 16,5:PRINT "DUMMY TEST OPTION:"   :LOCATE 16,33:PRINT TempCatch$ LOCATE 18,5:PRINT "SAVE PROGRAM"
LOCATE 19,5:PRINT "RETURN TO STAIRS TESTS LIST (ABANDON PROGRAM)"
LOCATE 20,5:PRINT "RETURN TO MAIN MENU (ABANDON PROGRAM)"

InputField%=1 :
ExitStEdit%=%False
DO UNTIL ExitStEdit%
   SELECT CASE InputField%
    . CASE 1 'NAME
         CALL Instruction(1,"input or modify test name")
        . CALL Instruction(2,"")
         CALL EngEdit(3,12,20,TempName$,ExitCode$)
      CASE 2 'description
         CALL Instruction(1,"input or modify test description")
         CALL Instruction(2,"")
         CALL EngEdit(4,12,40,TempDesc$,ExitCode$)
      CASE 3 'temp
         CALL Instruction(1,"input or modify adaptation temperature")
         CALL Instruction(2,"")
         CALL DecEdit(7,32,4,TempAdap$,ExitCode$)
      CASE 4 '
         CALL Instruction(1,"toggle WS/CS using TAB key")
         CALL Instruction(2,"WS = warm sensation    CS = cold sensation")
         LOCATE 8,34:COLOR 0,7
         IF TempMode%<>0 THEN Print Modality$(TempMode%) ELSE PRINT "  "
         CALL GetChar(ExitCode$,A$)
         IF ExitCode$="TAB" THEN INCR TempMode%
         IF TempMode%>2 THEN TempMode%=1
         LOCATE 8,34:COLOR 7,0
         IF TempMode%<>0 THEN Print Modality$(TempMode%) ELSE PRINT "  "
      CASE 5 '
         CALL Instruction(1,"input or modify temperature rate")
         CALL Instruction(2,"")
         CALL DecEdit(9,32,4,TempRate$,ExitCode$)
      CASE 6 '
         CALL Instruction(1,"input or modify time interval")
         CALL Instruction(2,"")
         CALL NatEdit(10,34,2,TempInt$,ExitCode$)
      CASE 7 '
         CALL Instruction(1,"input or modify step size")
         CALL Instruction(2,"")
         CALL DecEdit(11,32,4,TempFirst$,ExitCode$)
      CASE 8 '
         CALL Instruction(1,"input or modify step size")
         CALL Instruction(2,"")
         CALL DecEdit(12,32,4,TempSecond$,ExitCode$)
      CASE 9 '
         CALL Instruction(1,"input or modify step size")
         CALL Instruction(2,"")
         CALL DecEdit(13,32,4,TempThird$,ExitCode$)
```

```
CASE 10 '
   CALL Instruction(1,"toggle YES/NO using TAB key")
   CALL Instruction(2,"")
   CALL BinEdit(14,33,"YES"," NO",TempTrig$,ExitCode$)
CASE 11 '
   CALL Instruction(1,"toggle YES/NO using TAB key")
   CALL Instruction(2,"")
   CALL BinEdit(15,33,"YES"," NO",TempSound$,ExitCode$)
CASE 12 '
   CALL Instruction(1,"toggle YES/NO using TAB key")
   CALL Instruction(2,"")
   CALL BinEdit(16,33,"YES"," NO",TempCatch$,ExitCode$)
CASE 13 'save
   CALL Instruction(1,"")
   CALL Instruction(2,"")
   COLOR 0,7
   LOCATE 18,5:PRINT "SAVE PROGRAM"
   CALL GetChar(ExitCode$,A$)
   COLOR 7,0
   LOCATE 18,5:PRINT "SAVE PROGRAM"
 CASE 14'return to stairs menu
   CALL Instruction(1,"")
   CALL Instruction(2,"")
   COLOR 0,7
   LOCATE 19,5:PRINT "RETURN TO STAIRS TESTS LIST (ABANDON PROGRAM)"
   CALL GetChar(ExitCode$,A$)
   COLOR 7,0
   LOCATE 19,5:PRINT "RETURN TO STAIRS TESTS LIST (ABANDON PROGRAM)"
 CASE 15'return to main menu
   CALL Instruction(1,"")
   CALL Instruction(2,"")
   COLOR 0,7
   LOCATE 20,5:PRINT "RETURN TO MAIN MENU (ABANDON PROGRAM)"
   CALL GetChar(ExitCode$,A$)
   COLOR 7,0
   LOCATE 20,5:PRINT "RETURN TO MAIN MENU (ABANDON PROGRAM)"
END SELECT SELECT CASE ExitCode$
  CASE "UP"
    SELECT CASE InputField%
      CASE 2 TO 15
        DECR InputField%
    END SELECT
  CASE "DOWN"
    SELECT CASE InputField%
      CASE 1 TO 14
        INCR InputField%
    END SELECT CASE "CR"
    SELECT CASE InputField%
      CASE 1 TO 12
        INCR InputField%
      CASE 13 'SAVE 'TEST DATA
        DataTested%=%True
        IF TempName$ ="" THEN DataTested%=%False:InputField%=1
        IF VAL(TempAdap$)>35 OR VAL(TempAdap$)<25 THEN
           DataTested%=%False:InputField%=3
        END IF
        IF TempMode%=0 THEN  DataTested%=%False:InputField%=4
        IF VAL(TempRate$)=0 THEN DataTested%=%False:InputField%=5
        IF VAL(TempInt$)=0 THEN DataTested%=%False:InputField%=7

IF DataTested%=%True THEN
           StairsName$(StNr%)=TempName$
           StairsDesc$(StNr%)=TempDesc$
           StairsAdap%(StNr%)=VAL(TempAdap$)*10
           StairsMode%(StNr%)=TempMode%
           StairsRate%(StNr%)=VAL(TempRate$)*10
           StairsInt%(StNr%)=VAL(TempInt$)
           StairsFirst%(StNr%)=VAL(TempFirst$)*10
           StairsSecond%(StNr%)=VAL(TempSecond$)*10
           StairsThird%(StNr%)=VAL(TempThird$)*10
```

```
                IF TempTrig$=" NO" THEN
                    StairsTrig%(StNr%)=%False
                ELSE
                    StairsTrig%(StNr%)=%True
                END IF
                IF TempSound$=" NO" THEN
                    StairsSound%(StNr%)=%False
                ELSE
                    StairsSound%(StNr%)=%True
                END IF
                IF TempCatch$=" NO" THEN
                    StairsCatch%(StNr%)=%False
                ELSE
                    StairsCatch%(StNr%)=%True
                END IF
                IF StNr%>TotalStairs% THEN INCR TotalStairs%
                OPEN "STAIRS.TSA" FOR OUTPUT AS #1
                WRITE #1 ,TotalStairs%
                FOR I%=1 TO TotalStairs%
                    WRITE #1, StairsName$(I%),StairsDesc$(I%),StairsAdap%(I%)
                    WRITE #1,StairsMode%(I%),StairsRate%(I%),StairsInt%(I%)
                    WRITE #1,StairsFirst%(I%),StairsSecond%(I%),StairsThird%(I%)
                    WRITE #1,StairsTrig%(I%),StairsSound%(I%),StairsCatch%(I%)
                NEXT I%
                CLOSE #1
                ScreenCounter%=0
                ExitStEdit%=%True END IF
         CASE 14' return to stairs
            DECR ScreenCounter%
            ExitStEdit%=%True
         CASE 15
            ScreenCounter%=0
            ExitStEdit%=%True

END SELECT
    END SELECT
LOOP
END SUB

'FILE: TSA_LOGO.BAS

SUB Logo
SHARED Header$
L%=(58-LEN(Header$))\2
M%=58-L%-LEN(Header$)
LOCATE 1,2:PRINT CHR$(201);CHR$(205);" TSA ";STRING$(L%,205);
PRINT Header$;STRING$(M%,205);" MEDOC Ltd ";CHR$(205);CHR$(187);
FOR I%=2 TO 20
    LOCATE I%,2:PRINT CHR$(186);
    LOCATE I%,79:PRINT CHR$(186);
NEXT I%
LOCATE 21,2:PRINT CHR$(204);STRING$(31,205);
PRINT " INSTRUCTIONS ";STRING$(31,205);CHR$(185);
LOCATE 22,2:PRINT CHR$(186);:LOCATE 22,79:PRINT CHR$(186);
LOCATE 23,2:PRINT CHR$(186);:LOCATE 23,79:PRINT CHR$(186);
LOCATE 24,2:PRINT CHR$(200);STRING$(76,205);CHR$(188);

END SUB

'FILE: TSA_MAIN.BAS

%False=0 : %True= NOT %False
Done%=%False
StopStimulus%=%True
$INCLUDE "TSA_MENU.BAS"
$INCLUDE "NATEDIT.BAS"
$INCLUDE "DECEDIT.BAS"
$INCLUDE "ENGEDIT.BAS"
$INCLUDE "GETCHAR.BAS"
$INCLUDE "TSA_LOGO.BAS"
$INCLUDE "FAT_EDIT.BAS"
$INCLUDE "LIM_EDIT.BAS"
$INCLUDE "SEL_TEST.BAS"
$INCLUDE "RUN_LIM.BAS"
$INCLUDE "RUN_ST.BAS"
```

```
$INCLUDE "TSA_UTIL.BAS"
$INCLUDE "LIM_PRT.BAS"
$INCLUDE "CONTLOOP.BAS"
$INCLUDE "ST_EDIT.BAS"
$INCLUDE "FC_EDIT.BAS"

DIM MenuLine$(1:20),FirstMessage$(1:20),SecondMessage$(1:20)
DIM TestName$(1:15),TestDesc$(1:15)
DIM LimitsName$(1:15),LimitsDesc$(1:15),LimitsAdap%(1:15)
DIM LimitsMode%(1:15,0:6),LimitsRate%(1:15,1:6),LimitsStim%(1:15,1:6)
DIM LimitsInt%(1:15,1:6),LimitsTrig%(1:15,1:6),LimitsSound%(1:15,1:6)
DIM LimitsRand%(1:15,1:6),LimResults%(1:36)
DIM StairsName$(1:15),StairsDesc$(1:15),StairsAdap%(1:15)
DIM StairsMode%(1:15),StairsRate%(1:15),StairsInt%(1:15)
DIM StairsFirst%(1:15),StairsSecond%(1:15),StairsThird%(1:15)
DIM StairsTrig%(1:15),StairsSound%(1:15),StairsCatch%(1:15)
DIM StResults%(1:36)
DIM ForcedName$(1:15),ForcedDesc$(1:15),ForcedAdap%(1:15)
DIM ForcedMode%(1:15),ForcedRate%(1:15),ForcedInt%(1:15)
DIM ForcedFirst%(1:15),ForcedSecond%(1:15),ForcedThird%(1:15)
DIM ForcedTrig%(1:15),ForcedSound%(1:15),ForcedCatch%(1:15)
DIM FCResults%(1:36)
DIM TestSequence%(1:36)
DIM Index&(1:2000)
CLS
CALL Logo
CALL Instruction(1,"Please wait")
DIM Tout&(0:4096)
OUT 561,0
out 566,0                    ' reset AD
OUT 563,255                  ' start pump
' READ THERMISTOR TABLE
OPEN "VECO.TRM" FOR INPUT AS #1
FOR I% = 0 TO 4095
   INPUT #1,TT&
   IF I% MOD 100=0 THEN locate 22,50:PRINT I%
   Tout&(I%)=TT&*100
NEXT I%
CLOSE #1
locate 22,50:PRINT BIN$(INP(566))

ON TIMER(0.1) GOSUB 1000
TIMER ON
CALL Instruction(2,"loading LIMITS")
OPEN "LIMITS.TSA" FOR APPEND AS #1
FileLength%= LOF(1)
CLOSE #1
IF FileLength%>0 THEN
   OPEN "LIMITS.TSA" FOR INPUT AS #1
   INPUT #1 ,TotalLimits%
   FOR I%=1 TO TotalLimits%
      INPUT #1, LimitsName$(I%),LimitsDesc$(I%),LimitsAdap%(I%)
      FOR J% =1 TO 6
         INPUT #1,LimitsMode%(I%,J%),LimitsRate%(I%,J%),LimitsStim%(I%,J%)
         INPUT #1,LimitsInt%(I%,J%),LimitsTrig%(I%,J%),LimitsSound%(I%,J%)
         INPUT #1,LimitsRand%(I%,J%)
      NEXT J%
   NEXT I%
   CLOSE #1
END IF
CALL Instruction(2,"loading STAIRS")
OPEN "STAIRS.    " FOR APPEND AS #1
FileLength%= LOF(1)
CLOSE #1
IF FileLength%>0 THEN
   OPEN "STAIRS.TSA" FOR INPUT AS #1
   INPUT #1 ,TotalStairs%
   FOR I%=1 TO TotalStairs%
      INPUT #1, StairsName$(I%),StairsDesc$(I%),StairsAdap%(I%)
      INPUT #1,StairsMode%(I%),StairsRate%(I%),StairsInt%(I%)
      INPUT #1,StairsFirst%(I%),StairsSecond%(I%),StairsThird%(I%)
      INPUT #1,StairsTrig%(I%),StairsSound%(I%),StairsCatch%(I%)
   NEXT I%

CLOSE #1
END IF
CALL Instruction(2,"loading FORCED CHOICE")
```

```
OPEN "FORCED.TSA" FOR APPEND AS #1
FileLength%= LOF(1)
CLOSE #1
IF FileLength%>0 THEN
   OPEN "FORCED.TSA" FOR INPUT AS #1
   INPUT #1 ,TotalForced%
   FOR I%=1 TO TotalForced%
      INPUT #1, ForcedName$(I%),ForcedDesc$(I%),ForcedAdap%(I%)
      INPUT #1,ForcedMode%(I%),ForcedRate%(I%),ForcedInt%(I%)
      INPUT #1,ForcedFirst%(I%),ForcedSecond%(I%),ForcedThird%(I%)
      INPUT #1,ForcedTrig%(I%),ForcedSound%(I%),ForcedCatch%(I%)
   NEXT I%

CLOSE #1
END IF

OPEN "DEFAULT.TSA" FOR APPEND AS #1
FileLength%= LOF(1)
CLOSE #1
IF FileLength%>0 THEN
   OPEN "DEFAULT.TSA" FOR INPUT AS #1
   INPUT #1 ,DefaultMethod%,DefaultTestCode%,ExclusiveDefault%
   CLOSE #1
   SELECT CASE DefaultMethod%
      CASE 1  'LIMITS
         DefaultName$=LimitsName$(DefaultTestCode%)
      CASE 2  'T.S.L.
      CASE 3  'STAIRCASE
         DefaultName$=StairsName$(DefaultTestCode%)
      CASE 4  'FORCED CHOICE
      CASE 5  'SUPRATHRESHOLD
   END SELECT
ELSE
   'WILL BE USED IF DEFAULT FILE DOES NON EXIST
   DefaultMethod%=1:DefaultTestCode%=1:ExclusiveDefault%=%False
   DefaultName$=LimitsName$(1)
END IF CALL Instruction(2,"loading patients index")
OPEN "R",#1,"PATIENTS.TSA",34
FIELD #1,4 AS RecID$,_
         20 AS RecPatient$,_
         2 AS RecBirth$,_
         2 AS RecCode$ ,_
         2 AS RecD1$,_
         2 AS RecD2$,_
         2 AS RecD3$
TotalPatients% = INT(LOF(1)/34)
FOR I% = 1 TO TotalPatients%
   GET #1 , I%
   Index&(I%)=CVL(RecID$)
NEXT I%
CLOSE #1

ExitTsa%=%False
DO UNTIL ExitTsa%
   FOR I%=1 TO 20
      MenuLine$(I%)=""
      FirstMessage$(I%)="      USE "+CHR$(24)+CHR$(25)
      FirstMessage$(I%)=FirstMessage$(I%)+" KEYS TO SELECT. THEN PRESS <ENTER>"
      SecondMessage$(I%)=""
   NEXT I%
   Header$=" MAIN MENU "
   MenuLine$(7)="TEST                   "
   MenuLine$(9)="RETRIEVE TESTS DATA    "
   MenuLine$(11)="TESTS PROGRAMMING     "
   MenuLine$(13)="TESTS LIST            "
   MenuLine$(17)="END                   "
   FirstMessage$(17)="     WARNING !!! THIS CHOICE WILL TERMINATE THE PROGRAM !! "
   CLS
   CALL Logo
   CALL Menu(MainChoice%)
   SELECT CASE MainChoice%
```

```
CASE 7            '**** TEST ************

ScreenCounter%=1
   DO UNTIL ScreenCounter% = 0
     SELECT CASE ScreenCounter%
       CASE 1
         Header$ = " PATIENT ID "
         CLS:CALL Logo
         SearchID$=""
         CALL FindPatient(ActiveIndex%,ScreenCounter%,SearchID$)
       CASE 2
         IF ActiveIndex%>TotalPatients% THEN
           Header$ = " NEW PATIENT DATA "
         ELSE
           Header$ = " PATIENT DATA EDITING "
         END IF
         CLS:CALL Logo
         CALL Patientedit(ActiveIndex%,ScreenCounter%,SearchID$)
       CASE 3
         IF ExclusiveDefault%=%True THEN
           ScreenCounter% =5
         ELSE
           Header$ = " METHOD MENU "
   CLS:CALL Logo
   LOCATE 3,31:PRINT  STRING$(30,196);CHR$(191
   LOCATE 4,61 : PRINT CHR$(25)
   LOCATE 5,53:PRINT "DEFAULT TEST NAME:"
   LOCATE 7,53:PRINT DefaultName$
   CALL SelectMethod(MethodCode%,ScreenCounter%,"RUN")
   IF MethodCode% = 0 THEN
     MethodCode% = DefaultMethod%
     TestCode% = DefaultTestCode%
     ScreenCounter%=5
   END IF
   IF MethodCode% = 6 THEN ScreenCounter%=5 ' MANUAL TEST
 END IF
CASE 4
 SELECT CASE MethodCode%
   CASE 1 ' LIMITS
     FOR I%=1 TO TotalLimits%
       TestName$(I%)=LimitsName$(I%)
       TestDesc$(I%)=LimitsDesc$(I%)
     NEXT I%
     Total%=TotalLimits%
     Header$ = " LIMITS TESTS MENU "
   CASE 2
     Header$ = " T.S.L. TESTS MENU "
     FOR I%=1 TO TotalTSL%
       TestName$(I%)=TSLName$(I%)
       TestDesc$(I%)=TSLDesc$(I%)
     NEXT I%
     Total%=TotalTSL%
   CASE 3
     Header$ = " STAIRCASE TESTS MENU "
     FOR I%=1 TO TotalStairs%
       TestName$(I%)=StairsName$(I%)
       TestDesc$(I%)=StairsDesc$(I%)
     NEXT I%
     Total%=TotalStairs%
   CASE 4
     Header$ = " FORCED CHOICE TESTS MENU "
     FOR I%=1 TO TotalForced%
       TestName$(I%)=ForcedName$(I%)
       TestDesc$(I%)=ForcedDesc$(I%)
     NEXT I%
     Total%=TotalForced%
   CASE 5
     Header$ = " SUPRATHRESHOLD TESTS MENU "
     FOR I%=1 TO TotalSupra%
       TestName$(I%)=SupraName$(I%)
       TestDesc$(I%)=SupraDesc$(I%)
     NEXT I%
     Total%=TotalSupra%
 END SELECT
```

```
        CLS:  CALL Logo
        CALL SelTest(Total%,TestCode%,ScreenCounter%)
      CASE 5
        Header$ = " SITES MENU "
        CLS:  CALL Logo
        CALL SelectSite(SiteCode%,ScreenCounter%)
      CASE 6
        SELECT CASE SiteCode%
          CASE 1
            Header$ = " FACE LOCATIONS MENU "
          CASE 2
            Header$ = " TRUNK LOCATIONS MENU "
          CASE 3
            Header$ = " UPPER EXT. LOCATIONS MENU "
          CASE 4
            Header$ = " LOWER EXT. LOCATIONS MENU "
        END SELECT
        IF SiteCode% <> 5 THEN
          CLS:  CALL Logo
          CALL SelectLocation(SiteCode%,LocationCode%,ScreenCounter%)
        ELSE
          LocationCode% = 0 :INCR ScreenCounter%
        END IF
      CASE 7
        Header$=" SIDE SELECTION "
        CLS:  CALL Logo
        CALL SelectSide(SideCode%,ScreenCounter%)
      CASE 8
        CLS
        SCREEN 2
        SELECT CASE MethodCode%
          CASE 1 ' LIMITS
            CALL RunLimits
          CASE 2 ' T.S.L.
            cls:locate 10,25:print "PROGRAM NOT READY YET":DELAY 0.5
            ScreenCounter%=0 'while running program not ready yet
          CASE 3 ' STAIRCASE
            CALL RunStairs
          CASE 4 ' FORCED CHOICE
            cls:locate 10,25:print "PROGRAM NOT READY YET":DELAY 0.5
            ScreenCounter%=0 'while running program not ready yet
          CASE 5 ' SUPRATHRESHOLD
            cls:locate 10,25:print "PROGRAM NOT READY YET":DELAY 0.5
            ScreenCounter%=0 'while running program not ready yet
          CASE 6 ' MANUAL
            cls:locate 10,25:print "PROGRAM NOT READY YET":DELAY 0.5
            ScreenCounter%=0 'while running program not ready yet
        END SELECT
        SCREEN 0,0
      CASE 9
        Header$="POST TEST MENU"
        CLS:CALL Logo
        CALL PostMenu(ScreenCounter%)
    END SELECT
  LOOP

CASE 9 ' DATA RETREIVE

CASE 11 ' PROGRAM NEW TESTS/MODIFY EXISTING TESTS

ScreenCounter%=1
  DO UNTIL ScreenCounter% = 0
    SELECT CASE ScreenCounter%

CASE 1 'SELECT METHOD SCREEN

Header$ = " PROGRAMMING METHOD MENU "
      CLS:CALL Logo
      CALL SelectMethod(ProgramMethodCode%,ScreenCounter%,"PROGRAM")
      TempMethod%=ProgramMethodCode%
      IF ProgramMethodCode%=0 THEN
        CLS:Header$ = " DEFAULT METHOD MENU ":CALL Logo
        CALL SelectMethod(TempDefaultMethod%,ScreenCounter%,"DEFAULT")
        TempMethod%=TempDefaultMethod%
      END IF
```

```
CASE 2  ' TEST SELECTING SCREEN
  SELECT CASE TempMethod%
    CASE 1 'LIMITS
      FOR I%=1 TO 15
        TestName$(I%)=LimitsName$(I%)
        TestDesc$(I%)=LimitsDesc$(I%)
      NEXT I%
      Total%=TotalLimits%
      Header$ = " LIMITS TESTS MENU "
    CASE 2
      FOR I%=1 TO 15
        TestName$(I%)=TSLName$(I%)
        TestDesc$(I%)=TSLDesc$(I%)
      NEXT I%
      Total%=TotalTSL%
      Header$ = " T.S.L. TESTS MENU "
    CASE 3
      FOR I%=1 TO 15
        TestName$(I%)=StairsName$(I%)
        TestDesc$(I%)=StairsDesc$(I%)
      NEXT I%
      Total%=TotalStairs%
      Header$ = " STAIRCASE TESTS MENU "
    CASE 4
      FOR I%=1 TO 15
        TestName$(I%)=ForcedName$(I%)
        TestDesc$(I%)=ForcedDesc$(I%)
      NEXT I%
      Total%=TotalForced%
      Header$ = " FORCED CHOICE TESTS MENU "
    CASE 5
      FOR I%=1 TO 15
        TestName$(I%)=ForcedSupra$(I%)
        TestDesc$(I%)=ForcedSupra$(I%)
      NEXT I%
      Total%=TotalSupra
      Header$ = " SUPRATHRESHOLD TESTS MENU "
  END SELECT
  CLS:  CALL Logo
  IF ProgramMethodCode%>0 THEN
    IF Total% < 15 THEN
      TestName$(Total%+1)="NEW TEST":TestDesc$(Total%+1)=""
    END IF
  END IF
  CALL SelTest(Total%+1,TestCode%,ScreenCounter%)
CASE 3 ' PROGRAM EDITING SCREEN SELECT CASE ProgramMethodCode%
    CASE 0 ' SELECT EXCLUSIVE DEFAULT
    DefaultMethod%=TempDefaultMethod%
    DefaultTestCode%=TestCode%
    SELECT CASE DefaultMethod%
      CASE 1  'LIMITS
        DefaultName$=LimitsName$(DefaultTestCode%)
      CASE 2  'T.S.L.
      CASE 3  'STAIRCASE
        DefaultName$=StairsName$(DefaultTestCode%)
      CASE 4  'FORCED CHOICE
        DefaultName$=ForcedName$(DefaultTestCode%)
      CASE 5  'SUPRATHRESHOLD
    END SELECT
    IF ExclusiveDefault% =%True THEN A$="DISABLED" ELSE A$="ENABLED "
    CLS:LOCATE 10,20:PRINT"NON DEFAULT TESTS ARE ":CALL Logo
    CALL Instruction(1,"TOGGLE ENABLE/DISABLE USING <TAB> KEY")
    CALL Instruction(2,"RETURN TO MAIN MENU  USING <ENTER> KEY")
    ExitDefault%=%False
    DO UNTIL ExitDefault%
      CALL BinEdit(10,43,"DISABLED","ENABLED ",A$,ExitCode$)
      IF A$="DISABLED" THEN
        ExclusiveDefault% =%True
      ELSE
        ExclusiveDefault%=%False
      END IF
      IF ExitCode$=CE:" THEN ExitDefault%=%True
    LOOP
    CALL Instruction(1,"SAVING DEFAULT TEST DEFINITION")
    CALL Instruction(2,"")
```

```
              OPEN "DEFAULT.TSA" FOR OUTPUT AS #1
              WRITE #1 ,DefaultMethod%,DefaultTestCode%,ExclusiveDefault%
              CLOSE #1
              ScreenCounter% = 0
            CASE 1 ' EDIT LIMITS
              CLS:  Header$=" LIMITS PROGRAMMING SCREEN ":CALL Logo
              CALL LimEdit(TestCode%,ScreenCounter%)
            CASE 2 ' EDIT T.S.L.
              ScreenCounter%=0
            CASE 3 ' EDIT STAIRCASE
              CLS:  Header$=" STAIRS PROGRAMMING SCREEN ":CALL Logo
              CALL StEdit(TestCode%,ScreenCounter%)
            CASE 4 ' EDIT FORCED CHOICE
              CLS:  Header$=" FORCED CHOICE PROGRAMMING SCREEN ":CALL Logo
              CALL FCEdit(TestCode%,ScreenCounter%)
            CASE 5 ' EDIT SUPRATHRESHOLD
              ScreenCounter%=0
            END SELECT

END SELECT
        LOOP
      CASE 13

CASE 17
         ExitTsa%=%True
      END SELECT
LOOP
CLS:CALL Logo
LOCATE 10,40:PRINT "BYE-BYE"
END

1000

'READ A\D
    V1% = INP(560)
    V2% = INP(562)
    OUT 560,0
    IF V2%<17 THEN
       V%=256*V2%+V1%
     ELSE
       V%=4095
       print "busy"
    END IF 'STAND BY CONTROL LOOP ALGORITHM
    'SB=0.8*SB+Tout&(V%)/50000
    SB=Tout&(V%)/10000
    LOOPERROR=30-SB 'polarity fits pcb not ww
    A%=INT(5*LOOPERROR)

'OUTPUT TO PWM
    IF A%>127 THEN A% = 127
    IF A% < -127 THEN A% = -127
    A%=A%+128
    OUT 561,A%

RETURN

SUB Menu(MenuChoice%)
SHARED MenuLine$(),FirstMessage$(),SecondMessage$()
FOR I%=2 TO 20
  IF MenuLine$(I%)<>"" THEN LOCATE I%,10 : PRINT MenuLine$(I%)
NEXT I%
MenuChoice%=2 : FoundLine%=%False
DO UNTIL FoundLine%
   IF MenuLine$(MenuChoice%)<>"" THEN FoundLine% = %True ELSE INCR MenuChoice%
   IF MenuChoice%>20 THEN CLS:LOCATE .5,20:PRINT "NOT DEFINED MENU":STOP
LOOP
ChoiceDone%=%False
DO UNTIL ChoiceDone%
   LOCATE MenuChoice%,10
   COLOR 0,7 : PRINT MenuLine$(MenuChoice%) : COLOR 7,0
   LOCATE 22,3:PRINT FirstMessage$(MenuChoice%);
   PRINT STRING$(76-LEN(FirstMessage$(MenuChoice%)),32)
   LOCATE 23,3:PRINT SecondMessage$(MenuChoice%);
   PRINT STRING$(76-LEN(SecondMessage$(MenuChoice%)),32)
```

```
   KeyCode$=""
   DO UNTIL LEN(KeyCode$)<>0
        KeyCode$=INKEY$
   LOOP
   IF LEN(KeyCode$)=2 THEN
      KeyNumber%=ASC(RIGHT$(KeyCode$,1))
   ELSE
      KeyNumber%=ASC(KeyCode$)
   END IF
   LOCATE MenuChoice%,10
   PRINT MenuLine$(MenuChoice%)
   SELECT CASE KeyNumber%
      CASE 48,72
         I%=MenuChoice%:FoundLine%=%False
         DO UNTIL FoundLine%
            IF I%>2 THEN
               DECR I%
               IF MenuLine$(I%)<>"" THEN FoundLine% = %True :MenuChoice%=I%
            ELSE
               FoundLine% = %True
            END IF
         LOOP
      CASE 49,80
         I%=MenuChoice%:FoundLine%=%False
         DO UNTIL FoundLine%
            IF I%<20 THEN
               INCR I%
               IF MenuLine$(I%)<>"" THEN FoundLine% = %True:MenuChoice%=I%
            ELSE
               FoundLine% = %True
            END IF
         LOOP
      CASE 13
      ChoiceDone%=%True
   END SELECT
LOOP
END SUB
SUB SelectMethod (I%,C%,V$)
SHARED MenuLine$(),FirstMessage$(),SecondMessage$()
FOR II%=1 TO 20
   MenuLine$(II%)=""
   FirstMessage$(II%)="    USE "+CHR$(24)+CHR$(25)
   FirstMessage$(II%)=FirstMessage$(II%)+" KEYS TO SELECT. THEN PRESS <ENTER>"
   SecondMessage$(II%)=""
NEXT II%

MenuLine$(5)="LIMITS"
MenuLine$(7)="T.S.L."
MenuLine$(9)="STAIRCASE"
MenuLine$(11)="FORCED CHOICE"
MenuLine$(13)="SUPRATHRESHOLD"
MenuLine$(20)="RETURN TO MAIN MENU"
SELECT CASE V$
 CASE "RUN" ' TESTING
   MenuLine$(3)="DEFAULT TEST"
   MenuLine$(15)="MANUAL"
   MenuLine$(18)="RETURN TO PATIENT DATA EDITING"
 CASE "PROGRAM" ' PROGRAMING
   MenuLine$(3)="DEFAULT TEST"
END SELECT
CALL Menu(I%)
SELECT CASE I%
 CASE 3
   I%=0
 CASE 5,7,9,11,13,15
   I% = (I% - 3)\2 :INCR C%
 CASE 18
   DECR C%
 CASE 20
   I% = 99 : C% = 0
END SELECT
END SUB SUB SelectSite (I%,C%)
SHARED MenuLine$(),FirstMessage$(),SecondMessage$()
FOR II%=1 TO 20
```

```
   MenuLine$(II%)=""
   FirstMessage$(II%)="      USE "+CHR$(24)+CHR$(25)
   FirstMessage$(II%)=FirstMessage$(II%)+" KEYS TO SELECT. THEN PRESS <ENTER>"
   SecondMessage$(II%)=""
NEXT II%
MenuLine$(3)="FACE"
MenuLine$(5)="TRUNK"
MenuLine$(7)="UPPER EXTREMITY"
MenuLine$(9)="LOWER EXTREMITY"
MenuLine$(11)="OTHER"
MenuLine$(15)="RETURN TO TEST SELECTION"
MenuLine$(17)="RETURN TO MAIN MENU"
CALL Menu(I%)
SELECT CASE I%
 CASE 3,5,7,9,11
   I% = (I% - 1)\2 :INCR C%
 CASE 15
   I% = 0 : DECR C%
 CASE 17
   I% = 0 : C% = 0
END SELECT

END SUB

SUB SelectLocation (I%,J%,C%)
SHARED MenuLine$(),Message$,MenuHeader$,FirstMessage$(),SecondMessage$()
FOR II%=1 TO 20
   MenuLine$(II%)=""
   FirstMessage$(II%)="      USE "+CHR$(24)+CHR$(25)
   FirstMessage$(II%)=FirstMessage$(II%)+" KEYS TO SELECT. THEN PRESS <ENTER>"
   SecondMessage$(II%)=""
NEXT II%
MenuLine$(17)="RETURN TO SITE SELECTION"
MenuLine$(19)="RETURN TO MAIN MENU"
SELECT CASE I%
   CASE 1
      MenuLine$(3)="OPHTHALMIC"
      MenuLine$(5)="MAXILLARY"
      MenuLine$(7)="MANDIBULARY"
      CALL Menu(J%)
   CASE 2
      MenuLine$(3)="BACK"
      MenuLine$(5)="FRONT"
      CALL Menu(J%)
   CASE 3
      MenuLine$(3)="THENAR"
      MenuLine$(5)="HYPOTHENAR"
      MenuLine$(7)="HAND DORSUM"
      MenuLine$(9)="FINGERS"
      MenuLine$(11)="FOREARM"
      MenuLine$(13)="UPPER ARM"
      CALL Menu(J%)
   CASE 4
      MenuLine$(3)="FOOT DORSUM"
      MenuLine$(5)="FOOT PLANAR"
      MenuLine$(7)="LEG"
      MenuLine$(9)="THIGH"
      CALL Menu(J%)
END SELECT
SELECT CASE J%
 CASE 3,5,7,9,11,13
   J% = (J% - 1)\2 :INCR C%
 CASE 17
   J% = 0 : DECR C%
 CASE 19
   J% = 0 : C% = 0
END SELECT
END SUB SUB SelectSide (I%,C%)
SHARED MenuLine$(),Message$,MenuHeader$,FirstMessage$(),SecondMessage$()
FOR II%=1 TO 20
   MenuLine$(II%)=""
   FirstMessage$(II%)="      USE "+CHR$(24)+CHR$(25)
   FirstMessage$(II%)=FirstMessage$(II%)+" KEYS TO SELECT. THEN PRESS <ENTER>"
```

```
     SecondMessage$(II%)=""
NEXT II%
MenuLine$(3)="LEFT"
MenuLine$(5)="RIGHT"
MenuLine$(15)="RETURN TO LOCATION SELECTION"
MenuLine$(17)="RETURN TO MAIN MENU"
CALL Menu(I%)
SELECT CASE I%
  CASE 3,5
    I% = (I% - 1)\2 : INCR C%
  CASE 15
    I% = 0 : DECR C%
  CASE 17
    I% = 0 : C% = 0
END SELECT
END SUB SUB PostMenu(C%)
SHARED MenuLine$(),FirstMessage$(),SecondMessage$(),MethodCode%

FOR II%=1 TO 20
   MenuLine$(II%)=""
   FirstMessage$(II%)="    USE "+CHR$(24)+CHR$(25)
   FirstMessage$(II%)=FirstMessage$(II%)+" KEYS TO SELECT. THEN PRESS <ENTER>"
   SecondMessage$(II%)=""
NEXT II%
MenuLine$(3)="REPEATE TEST"
MenuLine$(5)="PRINT RESULTS"
MenuLine$(7)="PRINT RESULTS AND GRAPH"
MenuLine$(9)="ACCUMULATE RESULTS (NORM UPDATE)"
MenuLine$(18)="RETURN TO SITE SELECTION"
MenuLine$(20)="RETURN TO MAIN MENU"
CALL Menu(I%)
SELECT CASE I%
  CASE 3
    DECR C%
  CASE 5
    CLS
    SELECT CASE MethodCode%
      CASE 1
        CALL LimitsPrint
      CASE ELSE
        PRINT "PRINTING OF THIS METHOD NOT READY YET"
        DELAY .5
    END SELECT
  CASE 7
    CLS
    PRINT "PRINTING DEMO (WITH GRAPH)"
    DELAY 5
  CASE 9
    CLS
    PRINT "NORM UPDATE DEMO "
    DELAY 5

CASE 18
    C%=5
  CASE 20
    C% = 0
END SELECT
END SUB

SUB Instruction(I%,S$)

I$=RIGHT$(S$,76)
J%=LEN(I$)
K%=(76-J%)\2
L%=I%+21
LOCATE L%,3:PRINT  STRING$(K%,32);S$;STRING$((76-J%-K% ),32);

END SUB
```

ANNEX B

```
┌─ TSA ──────────────── MAIN MENU ──────────────── MEDOC Ltd ─┐
│                                                              │
│                                                              │
│    TEST                                                      │
│                                                              │
│    RETRIEVE TESTS DATA                                       │
│                                                              │
│    TESTS PROGRAMMING                                         │
│                                                              │
│    TESTS LIST                                                │
│                                                              │
│                                                              │
│    END                                                       │
│                                                              │
│                                                              │
├──────────────────── INSTRUCTIONS ───────────────────────────┤
│ KEYS TO SELECT. THEN PRESS <ENTER>                           │
└──────────────────────────────────────────────────────────────┘
```

```
┌─ TSA ──────────────── PATIENT ID ──────────────── MEDOC Ltd ─┐
│  * PATIENT ID NUMBER:                                         │
│                                                               │
│                                                               │
│                                                               │
│                                                               │
│                                                               │
│                                                               │
│    RETURN TO MAIN MENU                                        │
├──────────────────── INSTRUCTIONS ────────────────────────────┤
│       INPUT PATIENTS ID NUMBER USING NUMERIC KEYS             │
│           ERASE THE NUMBER USING <DEL> KEY                    │
└───────────────────────────────────────────────────────────────┘
```

```
┌─ TSA ──────────────── NEW PATIENT DATA ──────────────── MEDOC Ltd ─┐
│                                                                     │
│   * PATIENT ID NUMBER:    1002         LAST 3 TESTS DATES:          │
│                                                                     │
│     PATIENT NAME:        _                                          │
│                                                                     │
│     YEAR OF BIRTH:                                                  │
│                                                                     │
│     SEX:                                                            │
│                                                                     │
│                          DISEASES:                                  │
│                                                                     │
│    DIABETES:          UREMIA:              DRUG TOXITICITY          │
│                                                                     │
│    FAMILIAL NP:       RESERVED:            RESERVED                 │
│                                                                     │
│    RETURN TO MAIN MENU                                              │
│                                                                     │
│    CONTINUE                                                         │
├──────────────────────── INSTRUCTIONS ───────────────────────────────┤
│                                                                     │
└─────────────────────────────────────────────────────────────────────┘

┌─ TSA ──────────────── METHOD MENU ──────────────── MEDOC Ltd ─┐
│                                                                │
│   *   DEFAULT TEST                                             │
│                                                                │
│       LIMITS                       DEFAULT TEST NAME:          │
│                                                                │
│       T.S.L.                       SIMPLE                      │
│                                                                │
│       STAIRCASE                                                │
│                                                                │
│       FORCED CHOICE                                            │
│                                                                │
│       SUPRATHRESHOLD                                           │
│                                                                │
│       MANUAL                                                   │
│                                                                │
│       RETURN TO PATIENT DATA EDITING                           │
│                                                                │
│       RETURN TO MAIN MENU                                      │
├─────────────────────── INSTRUCTIONS ───────────────────────────┤
│ KEYS TO SELECT. THEN PRESS <ENTER>                             │
└────────────────────────────────────────────────────────────────┘

┌─ TSA ──────────────── SITES MENU ──────────────── MEDOC Ltd ─┐
│                                                               │
│   *   FACE                                                    │
│                                                               │
│       TRUNK                                                   │
│                                                               │
│       UPPER EXTREMITY                                         │
│                                                               │
│       LOWER EXTREMITY                                         │
│                                                               │
│       OTHER                                                   │
│                                                               │
│                                                               │
│       RETURN TO TEST SELECTION                                │
│                                                               │
│       RETURN TO MAIN MENU                                     │
│                                                               │
├─────────────────────── INSTRUCTIONS ──────────────────────────┤
│ KEYS TO SELECT. THEN PRESS <ENTER>                            │
└───────────────────────────────────────────────────────────────┘
```

```
┌─ TSA ──────────────── FACE LOCATIONS MENU ──────────────── MEDOC Ltd ─┐
│                                                                        │
│    •   OPHTHALMIC                                                      │
│                                                                        │
│        MAXILLARY                                                       │
│                                                                        │
│        MANDIBULARY                                                     │
│                                                                        │
│                                                                        │
│                                                                        │
│                                                                        │
│        RETURN TO SITE SELECTION                                        │
│                                                                        │
│        RETURN TO MAIN MENU                                             │
│                                                                        │
│ ─────────────────────── INSTRUCTIONS ────────────────────────          │
│ KEYS TO SELECT. THEN PRESS <ENTER>                           |         │
└────────────────────────────────────────────────────────────────────────┘

┌─ TSA ──────────────── TRUNK LOCATIONS MENU ─────────────── MEDOC Ltd ─┐
│                                                                        │
│    •   BACK                                                            │
│                                                                        │
│        FRONT                                                           │
│                                                                        │
│                                                                        │
│                                                                        │
│                                                                        │
│        RETURN TO SITE SELECTION                                        │
│                                                                        │
│        RETURN TO MAIN MENU                                             │
│                                                                        │
│ ─────────────────────── INSTRUCTIONS ────────────────────────          │
│ KEYS TO SELECT. THEN PRESS <ENTER>                           |         │
└────────────────────────────────────────────────────────────────────────┘

┌─ TSA ──────────────── UPPER EXT. LOCATIONS MENU ────────── MEDOC Ltd ─┐
│                                                                        │
│    •   THENAR                                                          │
│                                                                        │
│        HYPOTHENAR                                                      │
│                                                                        │
│        HAND DORSUM                                                     │
│                                                                        │
│        FINGERS                                                         │
│                                                                        │
│        FOREARM                                                         │
│                                                                        │
│        UPPER ARM                                                       │
│                                                                        │
│        RETURN TO SITE SELECTION                                        │
│                                                                        │
│        RETURN TO MAIN MENU                                             │
│                                                                        │
│ ─────────────────────── INSTRUCTIONS ────────────────────────          │
│ KEYS TO SELECT. THEN PRESS <ENTER>                           |         │
└────────────────────────────────────────────────────────────────────────┘
```

```
┌─ TSA ──────────── LOWER EXT. LOCATIONS MENU ──────────── MEDOC Ltd ─┐
│                                                                     │
│     · FOOT DORSUM                                                   │
│                                                                     │
│       FOOT PLANAR                                                   │
│                                                                     │
│       LEG                                                           │
│                                                                     │
│       THIGH                                                         │
│                                                                     │
│                                                                     │
│                                                                     │
│                                                                     │
│                                                                     │
│       RETURN TO SITE SELECTION                                      │
│                                                                     │
│       RETURN TO MAIN MENU                                           │
│                                                                     │
├──────────────────────── INSTRUCTIONS ───────────────────────────────┤
│ KEYS TO SELECT. THEN PRESS <ENTER>                              i   │
└─────────────────────────────────────────────────────────────────────┘

┌─ TSA ──────────────────── SIDE SELECTION ──────────────── MEDOC Ltd ─┐
│                                                                      │
│     · LEFT                                                           │
│                                                                      │
│       RIGHT                                                          │
│                                                                      │
│                                                                      │
│                                                                      │
│                                                                      │
│                                                                      │
│       RETURN TO LOCATION SELECTION                                   │
│                                                                      │
│       RETURN TO MAIN MENU                                            │
│                                                                      │
├──────────────────────── INSTRUCTIONS ────────────────────────────────┤
│ KEYS TO SELECT. THEN PRESS <ENTER>                              i    │
└──────────────────────────────────────────────────────────────────────┘
```

TEST NAME: SIMPLE

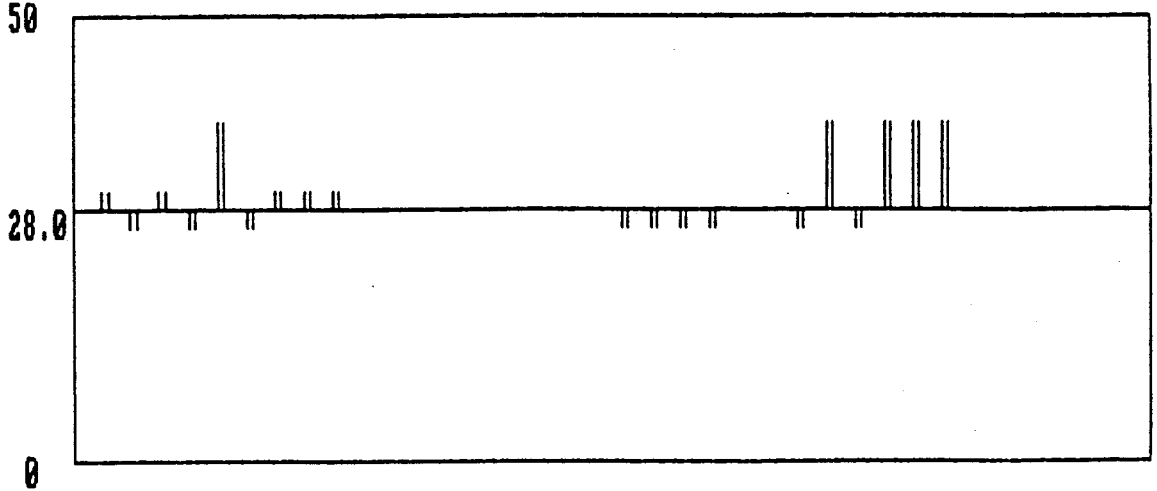

========== MOVE CURSOR TO CONTINUATION POINT ==========
TOUCH SPACEBAR TO START. PRESS ESC TO TERMINATE TEST

```
┌─ TSA ───────────────── POST TEST MENU ──────────────── MEDOC Ltd ─┐
│                                                                   │
│     REPEATE TEST                                                  │
│                                                                   │
│     PRINT RESULTS                                                 │
│                                                                   │
│     PRINT RESULTS AND GRAPH                                       │
│                                                                   │
│     ACCUMULATE RESULTS (NORM UPDATE)                              │
│                                                                   │
│                                                                   │
│                                                                   │
│                                                                   │
│     RETURN TO SITE SELECTION                                      │
│                                                                   │
│     RETURN TO MAIN MENU                                           │
├──────────────────────── INSTRUCTIONS ─────────────────────────────┤
│ KEYS TO SELECT. THEN PRESS <ENTER>                              i │
└───────────────────────────────────────────────────────────────────┘

┌─ TSA ──────────────── PROGRAMMING METHOD MENU ──────── MEDOC Ltd ─┐
│                                                                   │
│     DEFAULT TEST                                                  │
│                                                                   │
│     LIMITS                                                        │
│                                                                   │
│     T.S.L.                                                        │
│                                                                   │
│     STAIRCASE                                                     │
│                                                                   │
│     FORCED CHOICE                                                 │
│                                                                   │
│     SUPRATHRESHOLD                                                │
│                                                                   │
│                                                                   │
│                                                                   │
│     RETURN TO MAIN MENU                                           │
├──────────────────────── INSTRUCTIONS ─────────────────────────────┤
│ KEYS TO SELECT. THEN PRESS <ENTER>                              i │
└───────────────────────────────────────────────────────────────────┘

┌─ TSA ──────────────── DEFAULT METHOD MENU ──────────── MEDOC Ltd ─┐
│                                                                   │
│                                                                   │
│     LIMITS                                                        │
│                                                                   │
│     T.S.L.                                                        │
│                                                                   │
│     STAIRCASE                                                     │
│                                                                   │
│     FORCED CHOICE                                                 │
│                                                                   │
│     SUPRATHRESHOLD                                                │
│                                                                   │
│                                                                   │
│                                                                   │
│     RETURN TO MAIN MENU                                           │
├──────────────────────── INSTRUCTIONS ─────────────────────────────┤
│ KEYS TO SELECT. THEN PRESS <ENTER>                              i │
└───────────────────────────────────────────────────────────────────┘
```

```
┌ TSA ──────────────── LIMITS TESTS MENU ──────────────── MEDOC Ltd ┐
│       NAME                          DESCRIPTION                    │
│   SIMPLE              DEMO PROGRAM                                 │
│   PAIRS               3-PAIRS OF STIMULI INTERNALLY RANDOMIZED     │
│   NEW TEST                                                         │
│                                                                    │
│                                                                    │
│                                                                    │
│                                                                    │
│                                                                    │
│                                                                    │
│                                                                    │
│                                                                    │
│   RETURN TO METHOD SELECTION                                       │
│   RETURN TO MAIN MENU                                              │
│                       ──────── INSTRUCTIONS ────────               │
│                                                                    │
└────────────────────────────────────────────────────────────────────┘
```

```
┌ TSA ──────────────── LIMITS PROGRAMMING SCREEN ──────────── MEDOC Ltd ┐
│                                                                       │
1│ NAME:  SIMPLE                                                        │
2│ DESCR: DEMO PROGRAM                                                  │
│                                                                       │
3│ ADAPTATION TEMP:     26                                              │
│                                                                       │
4│ SEQUENCE Nr:         - 1 -    - 2 -    - 3 -    - 4 -    - 5 -    - 6 - │
5│ MODALITY:             HF       CS       WS       CS       CS       HF │
6│ TEMP RATE(deg/sec):   .5      1.3        1        1        1        1 │
7│ No OF STIMULI:         1        3        5        4        2        4 │
8│ INTERVAL (sec):       20        1        2        4        2        2 │
9│ MAN. TRIG. OPTION:   YES       NO       NO       NO       NO       NO │
10│ SOUND OPTION:        NO       NO      YES      YES      YES      YES │
11│ RANDOMIZE WITH NEXT: YES      YES       NO       NO      YES       NO │
│                                                                       │
│ SAVE PROGRAM                                                          │
│ RETURN TO LIMITS TESTS LIST (ABANDON PROGRAM)                         │
│ RETURN TO MAIN MENU (ABANDON PROGRAM)                                 │
│                          ──── INSTRUCTIONS ────                       │
│                      input or modify test name                        │
└───────────────────────────────────────────────────────────────────────┘
```

```
┌ TSA ──────────────── STAIRS PROGRAMMING SCREEN ──────────── MEDOC Ltd ┐
│                                                                       │
1│   NAME:  FAST STAIRS                                                 │
2│   DESCR: DEBUGING STAIRS PROGRAM                                     │
│                                                                       │
3│   ADAPTATION TEMP:          30                                       │
4│   MODALITY:                 CS                                       │
5│   TEMP RATE(deg/sec):        2                                       │
6│   INTERVAL (sec):            1                                       │
7│   COARSE SEARCH STEP         2                                       │
8│   INTERMEDIATE SEARCH STEP   1                                       │
9│   FINE SEARCH STEP          .5                                       │
10│   MAN. TRIG. OPTION:        NO                                       │
11│   SOUND OPTION:            YES                                       │
12│   DUMMY TEST OPTION:        NO                                       │
│                                                                       │
│   SAVE PROGRAM                                                        │
│   RETURN TO STAIRS TESTS LIST (ABANDON PROGRAM)                       │
│   RETURN TO MAIN MENU (ABANDON PROGRAM)                               │
│                          ──── INSTRUCTIONS ────                       │
│                      input or modify test name                        │
└───────────────────────────────────────────────────────────────────────┘
```

```
 ┌─ TSA ──────── FORCED CHOICE PROGRAMMING SCREEN ──────── MEDOC Ltd ─┐
1│  NAME:   FORCED NR 1
2│  DESCR:  PROGRAMMING DEMONSTRATION
 │
3│  ADAPTATION TEMP:         30.1
4│  MODALITY:                CS
5│  TEMP RATE(deg/sec):       .3
6│  INTERVAL (sec):          10
7│  COARSE SEARCH STEP        4
8│  INTERMEDIATE SEARCH STEP  2
9│  FINE SEARCH STEP          1
10│ MAN. TRIG. OPTION:       NO
11│ SOUND OPTION:            NO
12│ DUMMY TEST OPTION:       YES
 │
 │  SAVE PROGRAM
 │  RETURN TO FORCED CHOICE TESTS LIST (ABANDON PROGRAM)
 │  RETURN TO MAIN MENU (ABANDON PROGRAM)
 │  ──────────────── INSTRUCTIONS ────────────────
 │              input or modify test name
 └──────────────────────────────────────────────────────────────────┘
```

TEST NAME: stairs simple

```
50 ┌─────────────────────────────────────────────┐
   │                                             │
   │                                             │
30.5│─────────────────────────────────────────────│
   │ + + +                                       │
   │                                             │
   │                                             │
 0 └─────────────────────────────────────────────┘
    Y N Y !
    -0.5
      -0.5
        -0.5
```

TOUCH SPACEBAR TO START. PRESS ESC TO TERMINATE TEST

ANNEX C

LIMIT PROGRAMMING SCREEN INSTRUCTIONS 1) input or modify test name
2) input or modify test description
3) input or modify adaptation temperature
5) toggle modalities using TAB key
6) input or modify temperature rate
7) input or modify Number of stimuli
8) input or modify time interval
9) toggle YES/NO using TAB key
10) toggle YES/NO using TAB key
11) toggle YES/NO using TAB key

STAIRS PROGRAMMING SCREEN INSTRUCTION 1) input or modify test name
2) input or modify test description
3) input or modify adaptation temperature
4) toggle WS/CS using TAB key
5) input or modify temperature rate
6) input or modify time interval
7) input or modify step size
8) input or modify step size
9) input or modify step size
10) toggle YES/NO using TAB key
11) toggle YES/NO using TAB key
12) toggle YES/NO using TAB key

FORCED CHOICE PROGRAMMING SCREEN INSTRUCTION 1) input or modify test name
2) input or modify test description
3) input or modify adaptation temperature
4) toggle WS/CS using TAB key
5) input or modify temperature rate
6) input or modify time interval
7) input or modify step size
8) input or modify step size
9) input or modify step size
10) toggle YES/NO using TAB key
11) toggle YES/NO using TAB key
12) toggle YES/NO using TAB key

60

We claim:

1. Apparatus for measuring threshold sensitivity to a stimulus comprising:
sensory stimulation application means for providing stimulus to a subject;
computer means for governing operation of said sensory stimulation application means; and
operator interface means for interfacing between an operator and said computer means, said computer means and said operator interface means including means for enabling an operator to selectably apply said stimulus to a patient in accordance with the following protocols: method of limits; forced choice method; and staircase method, said operator interface means comprising:
display means;
means for indicating a test protocol in graphic form on said display means; and
means for indicating test results in graphic form on said display means.

2. Apparatus according to claim 1 and wherein:
said sensory stimulation application means comprises:
a probe including a first peltier element and first heat exchanger means;
means for supplying electrical power to the probe for heating of the first peltier element and including a temperature watch dog circuit a pulse width modulation circuit; and
means for circulating cooling fluid through said first heat exchanger means;
a second peltier element disposed remotely from said probe;
second heat exchanger means associated with said second peltier element;
means for circulating cooling fluid through said second heat exchanger means for providing cooling of said fluid; and
flexible cooling fluid conduit means interconnecting said first and second heat exchangers.

3. Apparatus according to claim 1 and wherein said computer apparatus and said operator interface apparatus includes means for enabling an operator to selectably apply said stimulus to a patient also in accordance with at least one of the following protocols: Thermal Sensitivity Limen (TSL) method and method of suprathreshold.

4. Apparatus according to claim 2 wherein said stimulus is heat applied to a desired location on said subject's body and wherein said sensory stimulation application means includes means for changing the temperature of said heat stimulus.

5. Apparatus according to claim 3 and wherein said means for changing said temperature can change said temperature at rates generally between 0.1° C./sec and 4° C./sec.

6. Apparatus according to claim 1 and also including means for performing age-normalized matching of results of a test.

7. Apparatus according to claim 1 and also including means for defining a new test protocol.

8. Apparatus according to claim 6 and wherein said means for defining a new test protocol includes means for defining a default test or series of tests.

9. Apparatus according to claim 1 and wherein each of said protocols includes a plurality of different trials and said operator interface means comprise means for selectably providing randomization of the order of said trials.

10. Apparatus for measuring threshold sensitivity to a stimulus comprising:
sensory stimulation application means for providing stimulus to a subject;
computer means for governing operation of said sensory stimulation application means; and
operator interface means for interfacing between an operator and said computer means,
said computer means and said operator interface means including means for enabling an operator to selectably apply said stimulus to a patient in accordance with the following protocols, each including a plurality of different trials:
method of limis; forced choice method; and staircase method,
said operator interface means comprising:
means for selectably providing randomization of the order of said trials.

11. Apparatus according to claim 10 and wherein each of said protocols includes a plurality of different trials and said operator interface means comprise means for selectably providing randomization of the order of said trials.

12. Apparatus according to claim 11 and wherein
said sensory stimulation application means comprises
a probe including a first peltier element and first heat exchanger means;
means for supplying electrical power to the probe for heating of the first peltier element and including a temperature watch dog circuit and a pulse width modulation circuit;
means for circulating cooling fluid through said first heat exchanger means;
a second peltier element disposed remotely from said probe;
second heat exchanger means associated with said second peltier element;
means for circulating cooling fluid through said second heat exchanger means for providing cooling of said fluid; and
flexible cooling fluid conduit means interconnecting said first and second heat exchangers.

* * * * *